(12) United States Patent
Budd et al.

(10) Patent No.: US 7,090,722 B2
(45) Date of Patent: *Aug. 15, 2006

(54) ACID-REACTIVE DENTAL FILLERS, COMPOSITIONS, AND METHODS

(75) Inventors: Kenton D. Budd, Woodbury, MN (US); Jason P. Thalacker, Minneapolis, MN (US); Sumita B. Mitra, West St. Paul, MN (US); Brant U. Kolb, Afton, MN (US); Lani S. Kangas, Woodbury, MN (US)

(73) Assignee: 3M Innovative Properties Company, St Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/847,805

(22) Filed: May 17, 2004

(65) Prior Publication Data
US 2005/0252415 A1 Nov. 17, 2005

(51) Int. Cl.
*A61F 2/00* (2006.01)
*A61K 6/06* (2006.01)
*A61K 6/08* (2006.01)
*A61K 6/083* (2006.01)

(52) U.S. Cl. ........................ 106/35; 501/151; 501/152; 423/263; 423/464; 423/465; 523/113; 523/115; 523/116

(58) Field of Classification Search ...................... None
See application file for complete search history.

(56) References Cited

U.S. PATENT DOCUMENTS

| | | |
|---|---|---|
| 4,209,434 A | 6/1980 | Wilson et al. |
| 4,259,075 A | 3/1981 | Yamauchi et al. |
| 4,298,738 A | 11/1981 | Lechtken et al. |
| 4,324,744 A | 4/1982 | Lechtken et al. |
| 4,356,296 A | 10/1982 | Griffith et al. |
| 4,385,109 A | 5/1983 | Lechtken et al. |
| 4,499,251 A | 2/1985 | Omura et al. |
| 4,503,169 A | 3/1985 | Randklev |
| 4,537,940 A | 8/1985 | Omura et al. |
| 4,539,382 A | 9/1985 | Omura et al. |
| 4,642,126 A | 2/1987 | Zador et al. |
| 4,652,274 A | 3/1987 | Boettcher et al. |
| 4,665,217 A | 5/1987 | Reiners et al. |
| 4,695,251 A | 9/1987 | Randklev |
| 4,710,523 A | 12/1987 | Lechtken et al. |
| 4,737,593 A | 4/1988 | Ellrich et al. |
| 4,752,338 A | 6/1988 | Reiners et al. |
| 4,772,530 A | 9/1988 | Gottschalk et al. |
| 4,798,814 A | 1/1989 | Everitt et al. |
| 4,871,786 A | 10/1989 | Aasen et al. |
| 4,872,936 A | 10/1989 | Engelbrecht |
| 4,874,450 A | 10/1989 | Gottschalk |
| 4,900,697 A | 2/1990 | Akahane et al. |
| 4,954,414 A | 9/1990 | Adair et al. |
| 4,954,462 A | 9/1990 | Wood et al. |
| 5,026,902 A | 6/1991 | Fock et al. |
| 5,037,579 A | 8/1991 | Matchett |
| 5,055,372 A | 10/1991 | Shanklin et al. |
| 5,057,393 A | 10/1991 | Shanklin et al. |
| 5,063,257 A | 11/1991 | Akahane et al. |
| 5,076,844 A | 12/1991 | Fock et al. |
| 5,130,347 A | 7/1992 | Mitra |
| 5,154,762 A | 10/1992 | Mitra et al. |
| 5,179,135 A | 1/1993 | Ellis et al. |
| 5,252,122 A | 10/1993 | Arnold |
| 5,332,429 A | 7/1994 | Mitra et al. |
| 5,350,782 A | 9/1994 | Sasaki et al. |
| 5,367,002 A | 11/1994 | Huang et al. |
| 5,372,796 A | 12/1994 | Wellinghoff |
| 5,501,727 A | 3/1996 | Wang et al. |
| 5,520,725 A | 5/1996 | Kato et al. |
| 5,530,038 A | 6/1996 | Yamamoto et al. |
| 5,545,676 A | 8/1996 | Palazzotto et al. |
| 5,609,675 A | 3/1997 | Noritake et al. |
| 5,670,583 A | 9/1997 | Wellinghoff |
| 5,694,701 A | 12/1997 | Huelsman et al. |
| 5,720,805 A | 2/1998 | Wellinghoff et al. |
| 5,859,089 A | 1/1999 | Qian |
| 5,883,153 A | 3/1999 | Roberts et al. |
| 5,925,715 A | 7/1999 | Mitra |
| 5,980,697 A | 11/1999 | Kolb et al. |
| 6,194,481 B1 | 2/2001 | Furman et al. |
| 6,214,101 B1 | 4/2001 | Nakaseko |
| 6,251,963 B1 | 6/2001 | Köhler et al. |
| 6,258,974 B1 | 7/2001 | Wellinghoff et al. |
| 6,262,142 B1 | 7/2001 | Wang et al. |
| 6,353,040 B1 | 3/2002 | Subelka et al. |
| 6,376,590 B1 | 4/2002 | Kolb et al. |
| 6,387,981 B1 | 5/2002 | Zhang et al. |

(Continued)

FOREIGN PATENT DOCUMENTS

DE 19753456 A1 6/1999

(Continued)

OTHER PUBLICATIONS

ASTM D 523-89 (Reapproved 1994) Standard Test Method for Specular Gloss.

(Continued)

*Primary Examiner*—C. Melissa Koslow
(74) *Attorney, Agent, or Firm*—Sean J. Edman

(57) ABSTRACT

Acid-reactive dental fillers, and methods of making and using such fillers, are disclosed. The acid-reactive dental fillers include a trivalent metal, oxygen, fluorine, an alkaline earth metal, and, optionally, silicon. The acid-reactive dental fillers are preferably nanostructured, for example, in the form of nanoparticles.

116 Claims, No Drawings

U.S. PATENT DOCUMENTS

| | | |
|---|---|---|
| 6,391,286 B1 | 5/2002 | Mitra et al. |
| 6,410,765 B1 | 6/2002 | Wellinghoff et al. |
| 6,417,244 B1 | 7/2002 | Wellinghoff et al. |
| 6,437,019 B1 | 8/2002 | Rusin et al. |
| 6,447,907 B1 | 9/2002 | Wolter et al. |
| 6,458,868 B1 | 10/2002 | Okada et al. |
| 6,540,978 B1 | 4/2003 | Margolskee |
| 6,566,413 B1 | 5/2003 | Weinmann et al. |
| 6,572,693 B1 | 6/2003 | Wu et al. |
| 6,620,861 B1 | 9/2003 | Nakatuka et al. |
| 6,624,236 B1 | 9/2003 | Bissinger et al. |
| 6,693,143 B1 | 2/2004 | Pflug |
| 6,695,617 B1 | 2/2004 | Wellinghoff et al. |
| 6,696,507 B1 | 2/2004 | Subelka et al. |
| 6,696,585 B1 | 2/2004 | Wellinghoff et al. |
| 2002/0013382 A1 | 1/2002 | Furman et al. |
| 2002/0193462 A1 | 12/2002 | Angeletakis et al. |
| 2003/0055123 A1 | 3/2003 | Kawashima et al. |
| 2003/0087986 A1 | 5/2003 | Mitra |
| 2003/0166737 A1 | 9/2003 | Dede et al. |
| 2003/0166740 A1 | 9/2003 | Mitra et al. |
| 2003/0166816 A1 | 9/2003 | Bissinger et al. |
| 2003/0180414 A1 | 9/2003 | Gudas et al. |
| 2003/0181541 A1 | 9/2003 | Wu et al. |
| 2003/0195273 A1 | 10/2003 | Mitra et al. |

FOREIGN PATENT DOCUMENTS

| | | |
|---|---|---|
| EP | 0 173 567 A2 | 3/1986 |
| EP | 0 201 031 A2 | 11/1986 |
| EP | 0 201 778 A1 | 11/1986 |
| EP | 0 201 778 B1 | 12/1988 |
| EP | 0 323 120 A2 | 7/1989 |
| EP | 0 323 120 A3 | 7/1989 |
| EP | 0 201 031 B1 | 8/1989 |
| EP | 0 373 384 B1 | 10/1992 |
| EP | 0 323 120 B1 | 3/1994 |
| EP | 0 373 384 A1 | 6/1996 |
| EP | 0 712 622 B1 | 9/1999 |
| EP | 1 051 961 A1 | 11/2000 |
| EP | 1066813 A | 1/2001 |
| EP | 1 269 968 A1 | 1/2003 |
| GB | 1316129 A | 5/1973 |
| JP | 05 331017 A | 12/1993 |
| JP | 06 321724 A | 11/1994 |
| JP | 2004 067597 A | 3/2004 |
| WO | 00/03688 A1 | 1/2000 |
| WO | 00/03747 A2 | 1/2000 |
| WO | 00/03747 A3 | 1/2000 |
| WO | 00/38619 A2 | 7/2000 |
| WO | 00/38619 A3 | 7/2000 |
| WO | 00/42092 A1 | 7/2000 |
| WO | 01/07444 A1 | 2/2001 |
| WO | 01/30305 A1 | 5/2001 |
| WO | 01/30306 A1 | 5/2001 |
| WO | 01/30307 A1 | 5/2001 |
| WO | 01/92271 A1 | 12/2001 |
| WO | WO 2002/096464 A1 | 12/2002 |
| WO | 03/063804 A1 | 8/2003 |
| WO | WO 2003/063804 | 8/2003 |
| WO | WO 2003/086328 A1 | 11/2003 |
| WO | WO 2004/043343 | 5/2004 |

OTHER PUBLICATIONS

U.S. Appl. No. 10/729,497 entitled "Compositions Including Polymerizable Bis-Phosphonic Acides and Methods," filed on Dec. 5, 2003.

U.S. Appl. No. 10/847,782 entitled "Dental Compositions Containing Nanozirconia Fillers," filed on May 17, 2004.

U.S. Appl. No. 10/847,781 entitled "Dental Compositions Containing Nanofillers and Related Methods," filed on May 17, 2004.

U.S. Appl. No. 10/847,803 entitled "Use of Nanoparticles to Adjust Refractive Index of Dental Compositions," filed on May 17, 2004.

U. S. Appl. No. 10/327,411 entitled "Dental Compositions Including Enzymes and Methods," filed on Dec. 20, 2002.

Stamboulis, et al., "Characterization of the structure of calcium alumino-silicate and calcium fluoro-alumino-silicate glasses by magic angle spinning nuclear magnetic resonance (MAS-NMR)" Journal of Non-Crystalline Solids, North-Holland Physics Publishing, Amsterdam, NL, vol. 333, No. 1, Jan. 1, 2004, pp. 01-107, XP004479772, ISSN: 0022-3093 abstract.

Keast Russell S J, et al: "Modifying the Bitterness of Selected Oral Pharmaceuticals with Cation and Anion Series of Salts" Database Biosis Online! Biosciences Infromation Service, Philadelphia, PA US: Jul. 2002 (Jul. 2002 XP002331214 Database accession No. PREV200200479568 Abstract & Pharmaceutical Research (new York), vol. 19, No. 7, (Jul. 2002), pp. 1019-1026, ISNN: 0724-8741.

ACID-REACTIVE DENTAL FILLERS, COMPOSITIONS, AND METHODS

BACKGROUND

Acid-reactive fillers have been widely used in dental compositions. Acid-reactive fillers include, for example, metal oxides, metal salts, and glasses. An example of an acid-reactive glass is fluoroaluminosilicate (FAS) glass, which is a known fluoride releasing material. FAS glass particles are typically prepared by a melt fusion process, which effectively limits available particle sizes to particles typically having an average size of at least 0.5 micrometers.

For applications in which the acid-reactive filler is dispersed in a hardenable resin to form a dental composition (e.g., a dental paste), the reactivity of the acid-reactive filler in the composition is generally limited by the available surface area of the acid-reactive filler. Thus, high loadings (e.g., greater than 50% by weight) of acid-reactive filler are often used to achieve compositions with the desired level of reactivity. However, high loadings of acid-reactive fillers sometimes restrict the flexibility to incorporate additional fillers (e.g., non acid-reactive fillers) in the composition.

As such, there remains a need for acid-reactive dental fillers with improved properties including, for example, higher surface areas.

SUMMARY

In one aspect, the present invention provides a composition that is a dental filler, and methods of making and using such dental fillers. In one embodiment, the dental filler includes an oxyfluoride material that is acid-reactive, non-fused, and includes a trivalent metal, oxygen, fluorine, and an alkaline earth metal. Preferably the trivalent metal includes aluminum and/or lanthanum, and in more preferred embodiments the trivalent metal is aluminum. In some embodiments, the oxyfluoride material optionally includes silicon and/or a heavy metal. Preferably at least a portion of the oxyfluoride material is nanostructured.

In another embodiment, the dental filler includes an oxyfluoride material that is acid-reactive, and includes a trivalent metal, oxygen, fluorine, and an alkaline earth metal, with the proviso that the oxyfluoride material includes at most 25 mole %, and preferably at most 20 mole % silicon, based on the total moles of silicon, trivalent metal, alkaline earth metal, and any additional cations.

In another aspect, the present invention provides dental compositions, and methods of making and using dental compositions, wherein the dental composition includes a dental filler of the present invention and a hardenable resin (e.g., a polymerizable ethylenically unsaturated compound and/or an acid). The dental composition may be a single-part or a multi-part dental composition. In addition to the dental filler of the present invention, such dental compositions can include additional acid-reactive or non acid-reactive fillers including, for example, nanofillers. The dental compositions of the invention may be dental adhesives, cavity liners, cements, coating, orthodontic adhesives, restoratives, sealants, and combinations thereof. Dental compositions of the present invention can be hardened to prepare dental articles including, for example, crowns, fillings, mill blanks, orthodontic devices, and prostheses.

Preferably, by incorporating acid-reactive fillers of the present invention in resins, dental compositions (e.g., dental restoratives) can be prepared that exhibit improvements in one or more properties including, for example, strength, polish, polish retention, fluoride release, abrasion resistance, aesthetics, and radiopacity.

Definitions

As used herein, a "non-fused" material means that the material was not formed from a melted state. Non-fused materials may be formed by methods including, for example, chemical syntheses, precipitations, and combinations thereof.

As used herein, a "dental filler" is a particulate material suitable for use in the oral environment. Dental fillers generally have an average particle size of at most 100 micrometers.

As used herein, the term "paste" refers to a soft, viscous mass of solids dispersed in a liquid.

As used herein, the term "non-fused" refers to a material that has not been prepared by a melt fusion process.

As used herein, an "acid-reactive" dental filler is a filler that chemically reacts in the presence of an acidic component.

As used herein, an "alkaline earth metal" is an element selected from the group consisting of Be, Mg, Ca, Sr, and Ba.

As used herein an oxyfluoride is a material in which atoms of oxygen and fluorine are bonded to the same atom (e.g., aluminum in an aluminum oxyfluoride). Generally, at least 50% of the fluorine atoms are bonded to an atom bearing an oxygen atom in an oxyfluoride material.

As used herein, a "nanostructured" material refers to a material in a form having at least one dimension that is, on average, at most 200 nanometers (e.g., nanosized particles). Thus, nanostructured materials refer to materials including, for example, nanoparticles as defined herein below; aggregates of nanoparticles; materials coated on particles, wherein the coatings have an average thickness of at most 200 nanometers; materials coated on aggregates of particles, wherein the coatings have an average thickness of at most 200 nanometers; materials infiltrated in porous structures having an average pore size of at most 200 nanometers; and combinations thereof. Porous structures include, for example, porous particles, porous aggregates of particles, porous coatings, and combinations thereof.

As used herein, "nanoparticles" is used synonymously with "nanosized particles," and refers to particles having an average size of at most 200 nanometers. As used herein for a spherical particle, "size" refers to the diameter of the particle. As used herein for a non-spherical particle, "size" refers to the longest dimension of the particle.

As used herein, "agglomerated" is descriptive of a weak association of primary particles usually held together by charge or polarity. Agglomerated particles can typically be broken down into smaller entities by, for example, shearing forces encountered during dispersion of the agglomerated particles in a liquid.

In general, "aggregated" and "aggregates" are descriptive of a strong association of primary particles often bound together by, for example, residual chemical treatment, covalent chemical bonds, or ionic chemical bonds. Further breakdown of the aggregates into smaller entities is very difficult to achieve. Typically, aggregated particles are not broken down into smaller entities by, for example, shearing forces encountered during dispersion of the aggregated particles in a liquid.

As used herein, "aggregated silica" is descriptive of an association of primary silica particles often bound together by, for example, residual chemical treatment, covalent chemical bonds, or ionic chemical bonds. Although complete breakdown of aggregated silica into smaller entities may be difficult to achieve, limited or incomplete breakdown may be observed under conditions including, for example, shearing forces encountered during dispersion of the aggregated silica in a liquid. As used herein, a "silica cluster" or "silica-zirconia cluster" refers to aggregated silica or silica-zirconia in which a substantial amount of the aggregated primary silica or zirconia particles are loosely bound. "Loosely bound" refers to the nature of the association among the particles present in the silica or silica-zirconia cluster. Typically, the particles are associated by relatively weak intermolecular forces that cause the particles to clump together. Preferably, many of the clusters remain intact during dispersion into a hardenable resin for a dental material, even though some clusters may be fractured into smaller structures during the dispersion process. Thus, silica clusters and silica-zirconia clusters are typically referred to as "loosely bound aggregated silica" or "loosely bound aggregated silica-zirconia." The clusters disclosed in the present application are preferably substantially spherical and preferably not fully densified. The term "fully dense," as used herein, is descriptive of a particle that is near theoretical density, having substantially no open porosity detectable by standard analytical techniques such as the B.E.T. nitrogen technique (based upon adsorption of $N_2$ molecules from a gas with which a specimen is contacted). Such measurements yield data on the surface area per unit weight of a sample (e.g. $m^2/g$), which can be compared to the surface area per unit weight for a mass of perfect microspheres of the same size to detect open porosity. The term "not fully densified" as used herein, is descriptive of a particle that is less than theoretical density, and therefore, has porosity. For porous particles with open porosity, (e.g., clusters of primary particles), the measured surface area is greater than the surface area calculated for solid particles of the same size. Such measurements may be made on a Quantasorb apparatus made by Quantachrome Corporation of Syossett, N.Y. Density measurements may be made using an air, helium or water pycnometer.

As used herein, "particle size" refers to the longest dimension (e.g., diameter) of a particle.

Silica clusters disclosed in the present application may be manufactured in a process that includes drying and optionally heat treating and/or calcining. The ratio of the surface area after heat treatment compared to the surface area before heat treatment is preferably greater than 50%, more preferably greater than 80%. Preferably the change in surface area after heating is at most 10% and more preferably at most 5%.

As used herein, a "shelf-stable" composition refers to a composition that has a shelf-life of at least one year, and preferably at least 2 years, at room temperature. Shelf-life of an adhesive composition is typically measured by determining if the aged composition provides acceptable bond strengths when the aged composition is bonded to a dental structure surface.

DETAILED DESCRIPTION OF PREFERRED EMBODIMENTS

The present invention provides a dental filler that includes an acid-reactive oxyfluoride material, and methods of making and using the dental filler. As used herein an oxyfluoride is a material in which atoms of oxygen and fluorine are bonded to the same atom (e.g., aluminum in an aluminum oxyfluoride). In some embodiments, at least 50%, sometimes at least 70%, and in other embodiments at least 80%, of the fluorine atoms are bonded to or coordinated by an atom bearing or coordinated by an oxygen atom in an oxyfluoride material. Single- and multi-part dental compositions can include, in addition to a dental filler of the present invention, a hardenable resin and/or a hardenable polyacid. Such dental compositions are useful as, for example, dental adhesives, artificial crowns, anterior fillings, posterior fillings, casting materials, cavity liners, cements, coating compositions, mill blanks, orthodontic devices, orthodontic adhesives, restoratives, prostheses, and sealants.

Dental Fillers Including Acid-Reactive, Oxyfluoride Materials

The present invention provides a composition including an acid-reactive, oxyfluoride material that is a dental filler. The oxyfluoride material includes a trivalent metal, oxygen, fluorine, and an alkaline earth metal. Preferably the trivalent metal is aluminum, lanthanum, or combinations thereof. More preferably the trivalent metal is aluminum. Preferably the alkaline earth metal is strontium, calcium, barium, or combinations thereof. In some embodiments of the present invention, the oxyfluoride material may further include silicon and/or heavy metal (e.g., zirconium, lanthanum, niobium, yttrium, or tantalum), or more specifically, oxides, fluorides and/or oxyfluorides thereof. In some embodiments, the oxyfluoride material includes at most 25 mole % silicon, and preferably at most 20 mole % silicon, based on the total moles of silicon, the trivalent metal, the alkaline earth metal, and any additional cations in the oxyfluoride material. In other embodiments, the oxyfluoride material is non-fused.

The molar ratio of the trivalent metal to the alkaline earth metal in the oxyfluoride material can affect chemical and structural properties including, for example, acid reactivity and efficiency in the hardening reaction of acid-reactive fillers with polyacids. For example, increasing the alkaline earth metal content can result in greater acid reactivity. However, for some embodiments trivalent metal content sufficient to promote the formation of relatively homogeneous oxyfluoride structures is preferred. Increasing the trivalent metal content can increase the efficiency of the oxyfluoride material in hardening polyacids, which can allow one of skill in the art to eliminate or reduce the use of conventional FAS filler in certain dental compositions. In some embodiments, the molar ratio of the trivalent metal to the alkaline earth metal in the oxyfluoride material is at least 50:50, and in other embodiments at least 70:30. In some embodiments, the molar ratio of the trivalent metal to the alkaline earth metal in the oxyfluoride material is at most 95:5, and in other embodiments at most 90:10.

The ratio of oxygen to fluorine in the oxyfluoride material can affect the physical characteristics and the reactivity of the filler. Typically, increasing the fluoride content of the oxyfluoride materials results in precipitated fillers having decreased surface area, increased primary particle size, and decreased acid reactivity. However, substantial fluorine content is desirable to provide fluoride release from certain dental compositions, and some fluorine is typically required for optimum reactivity. In some embodiments, the molar ratio of oxygen to fluorine in the oxyfluoride material is at least 50:50, sometimes at least 60:40, and in other embodiments at least 65:35. In some embodiments, the molar ratio of oxygen to fluorine in the oxyfluoride material is at most 95:5, sometimes at most 90:10, and in other embodiments at most 85:15.

In some embodiments of the present invention, at least a portion of the oxyfluoride material is nanostructured. Such nanostructured materials include the oxyfluoride material in the form of, for example, nanoparticles, coatings on particles, coatings on aggregates of particles, infiltrate in a porous structure, and combinations thereof. Preferably at least 90% by weight, more preferably at least 95% by weight, and most preferably at least 98% by weight of the oxyfluoride material is nanostructured.

In some embodiments of the present invention, at least a portion of the nanostructured oxyfluoride material can be in the form of aggregated or non-aggregated nanoparticles. In such embodiments, preferably at least 90% by weight, more preferably at least 95% by weight, and most preferably at least 98% by weight of the oxyfluoride material is in the form of nanoparticles. Preferably the nanoparticles have an average size of at most 100 nanometers, more preferably at most 50 nm, even more preferably at most 20 nm.

In embodiments in which the oxyfluoride material is in the form of nanoparticles, the oxyfluoride material preferably has a surface area of at least 10 square meters per gram ($m^2/g$), more preferably at least 25 $m^2/g$, and most preferably at least 50 $m^2/g$.

In some embodiments of the present invention, the nanostructured oxyfluoride material can be in the form of a coating on a particle (e.g., a nanoparticle). Suitable particles include, for example, metal oxide particles (e.g., silica, zirconia, alumina, titania, yttrium oxide, lanthanum oxide and mixed metal oxides including, for example, zirconate or titanate perovskites), glass particles (e.g., dental glass), non-oxide particles (e.g., colloidal metal fluorides such as yttrium fluoride), and combinations thereof.

Coatings can be advantageously formed on conventional size filler particles, nanoparticles, and aggregates. Suitable conventional particles typically have an average size of at least 0.5 micrometer, and often at least 1 micrometer. Suitable conventional particles typically have an average size of at most 50 micrometers, and often at most 10 micrometers.

The average coating thickness is typically at least 20 nanometers, and often at least 50 nanometers. The average coating thickness is typically at most 1000 nanometers, and often at most 500 nanometers.

In some embodiments of the present invention, the nanostructured oxyfluoride material can be in the form of a coating on an aggregate of particles (e.g., an aggregate of nanoparticles). Suitable particles include, for example, metal oxide particles (e.g., silica, zirconia, alumina, titania, yttrium oxide, lanthanum oxide and mixed metal oxides including, for example, zirconate or titanate perovskites), glass particles (e.g., dental glass), non-oxide particles (e.g., colloidal metal fluorides such as yttrium fluoride), and combinations thereof.

Suitable aggregates can be similar in size to conventional fillers (e.g., at least 1 micrometer in some embodiments, and at most 10 micrometers in other embodiments). Useful aggregates of particles smaller than conventional fillers (e.g., nanofillers) typically have a size of at least 50 nanometers in some embodiments, and at most 1 micrometer in other embodiments. The average coating thickness is typically at least 20 nanometers in some embodiments, and often at most half the aggregate size in other embodiments.

In some embodiments of the present invention, the nanostructured oxyfluoride material can be in the form of an infiltrate in a porous structure (e.g., a porous particle, a porous aggregate of particles, a porous coating, or a combination thereof). In embodiments in which the porous structure includes porous particles, the porous particles can include, for example, metal oxide particles (e.g., silica, zirconia, alumina, titania, yttrium oxide, lanthanum oxide and mixed metal oxides including, for example, zirconate or titanate perovskites), glass particles (e.g., dental glass), non-oxide particles (e.g., colloidal metal fluorides such as yttrium fluoride), and combinations thereof. In embodiments in which the porous structure includes a porous aggregate of particles, the particles are preferably nanoparticles. Preferably the average pore size is at least 20 nanometers, and more preferably at least 50 nanometers. Preferably the average pore size is at most 10 micrometers, and more preferably at most 1000 nanometers.

Particles and coatings can be combined to provide dental fillers of the present invention. For example, a porous coating can be formed on conventional filler particles, and infiltrated with the oxyfluoride material of the present invention. Such a structure might include, for example, a dental glass with a colloidal silica coating.

Dental fillers of the present invention include an acid-reactive oxyfluoride material. Preferably the acid-reactive oxyfluoride material can react with an acidic material (e.g., organic acid, inorganic acid, monomeric acid, oligomeric acid, and polymeric acid), and preferably a polyacid as described herein. Typically, dental fillers of the present invention undergo significant surface corrosion or dissolution when exposed to various acids used in dental compositions, such as poly(meth)acrylic acids or phosphonic acids. The corroded or dissolved filler releases fluoride ions into the surrounding liquid or matrix. Multivalent cations useful in curing ionomers are also released. Typically, significant surface corrosion or dissolution occurs at or near body temperature when acid-reactive fluoride materials are contacted with acids commonly used in dental compositions.

Preparations of Dental Fillers

The present invention provides methods of preparing dental fillers including an acid-reactive oxyfluoride material including a trivalent metal, oxygen, fluorine, and an alkaline earth metal.

In one embodiment, the method includes combining a first liquid composition and a second liquid composition, and separating (e.g., filtering) the oxyfluoride material from the combined liquids. The first liquid composition includes a source of a trivalent metal and a source of an alkaline earth metal. The second liquid composition includes a source of fluorine, and optionally, a source of silicon.

Preferably the trivalent metal is aluminum, lanthanum, or combinations thereof. More preferably, the trivalent metal is aluminum. Preferably at least one of the liquid compositions further includes a source of hydroxide as a source of oxygen.

Optionally, at least one of the first or second liquid compositions can include water. Typically at least one of the liquid compositions is an aqueous composition having a pH greater than 7, sometimes having a pH greater than 9.

The first liquid composition includes a source for a trivalent metal. Sources for trivalent metals include, for example, trivalent metal salts and alkoxides. Suitable salts include, for example, lanthanum nitrates and basic or oxy salts thereof, lanthanum carboxylates and basic or oxy salts thereof, lanthanum halides and basic or oxy salts thereof, aluminum nitrates and basic or oxy salts thereof, aluminum carboxylates and basic or oxy salts thereof, aluminum halides and basic or oxy salts thereof, and combinations thereof. Suitable alkoxides include, for example, lanthanum isopropoxide, lanthanum sec-butoxide, aluminum isopropoxide, aluminum sec-butoxide, and combinations thereof.

The concentration of the trivalent metal salt should be low enough to readily promote full dissolution. More dilute solutions are sometimes useful for promoting fine precipitates. The volume of anion solution is a significant portion of the total reaction volume in many embodiments. Typically, the concentration of the trivalent metal source in the first liquid composition is at least 0.1 molar, and in other embodiments at most 2.5 molar.

The first liquid composition also includes a source for an alkaline earth metal. Suitable sources for alkaline earth metals include, for example, strontium nitrates, strontium carboxylates, strontium halides, calcium nitrates, calcium carboxylates, calcium halides, and combinations thereof. Typically, the concentration of the alkaline earth metal source in the first liquid composition is at least 0.1 molar, and in other embodiments at most 2.5 molar.

The molar ratio of trivalent to divalent cations in the reaction product is typically about the same as that in the combined cation solution prior to precipitation. In many embodiments, the preferred ratio in the solution is the same as the preferred ratio in the filler.

The second liquid composition includes a source for fluorine. Suitable sources for fluorine include, for example, ammonium fluoride, ammonium hydrogen difluoride, hexafluorosilicic acid and salts thereof, and combinations thereof. Dilute solutions tend to promote the precipitation of fine particles, whereas concentrated solutions can result in easier separation and recovery of the precipitated filler. Typically, the fluorine concentration is at least 0.1 molar, and in some embodiments at most 5 moles per liter.

Optionally, at least one of the first or second liquid compositions can include a source of hydroxide as a source of oxygen. Suitable hydroxide sources include, for example, ammonium hydroxide, sodium hydroxide, potassium hydroxide, and combinations thereof.

The amount of second liquid composition (i.e., fluorine containing liquid) is the amount that results in the desired fluoride content of the filler. When both fluoride and hydroxide are present in the second liquid, a two to three times stoichiometric excess (e.g., 9 moles of combined fluoride and hydroxide for every mole of trivalent aluminum is 3 times the stoichiometric amount) is typically used to ensure complete reaction with and precipitation of the cations in the first liquid composition. The fluorine content in the filler is determined by the F:OH ratio, not simply the total F in the second liquid. The ratio of F:O in the filler is not necessarily equal to the ratio of F:OH in the solutions and depends on the reaction chemistry of specific cation solutions. The ratio in solution required to give a desired fluorine content can be readily determined by one of skill in the art with guidance from the Examples described herein.

Optionally, the second liquid composition includes a source for silicon. Suitable sources for silicon include, for example, sodium silicate, hexafluorosilicic acid and salts thereof, silicon alkoxides, and combinations thereof.

If present, the concentration of the silicon source in the second liquid composition is generally similar to the concentration of fluoride and hydroxide described herein above. Useful concentrations of silicon are typically sufficient to provide the desired number of silicon atoms in relation to number of divalent and trivalent atoms in the first liquid composition.

In some embodiments in which silicon is present, preferably the silicon source is present in an amount sufficient to provide an oxyfluoride material including at most 25 mole % silicon, and more preferably at most 20 mole % silicon, based on the total moles of silicon, the trivalent metal, the alkaline earth metal, and any additional cations in the oxyfluoride material.

Preferably the first and second liquid compositions are combined under conditions including efficient agitation (e.g., rapid stirring). For example, the first liquid composition can be added to a vessel containing the second liquid composition with rapid stirring. Typically precipitation is rapid, but agitation can be continued (e.g., for 10 minutes or more in some embodiments, for 60 minutes or more in other embodiments) to ensure complete reaction.

Typically, the reaction is carried out at or near room temperature, but higher or lower temperatures can be used as desired in certain embodiments.

The oxyfluoride material may be separated from the combined liquids by methods known in the art including, for example, filtration, centrifugation, settling, decanting, and combinations thereof. Preferably the oxyfluoride material is filtered. Upon separation, the oxyfluoride can optionally be washed using suitable liquids including, for example, water, alcohols, and combinations thereof.

The method may optionally include drying the separated oxyfluoride material at a temperature of at most 350° C., more preferably at most 250° C., and most preferably at most 150° C. Suitable drying methods are known in the art and include, for example, hot air drying (e.g., oven drying).

Preferably the method provides the oxyfluoride material in a form of, for example, a precipitate, a coating on a particle, a coating on an aggregate of particles, a material infiltrated into a porous structure, or combinations thereof. Optionally, the oxyfluoride material can be redispersed in a liquid medium (e.g., a medium including water) after separation or after drying. Oxyfluoride material particularly useful for dispersion in a dental composition can be formed by milling dried or separated material. Milling can be done in water or other liquids, or can be done in the presence of dental resins or other components.

Methods known in the art for milling ceramic or inorganic particles, including ball milling, attritor or fluid energy mills, jets mills, and the like are suitable for milling oxyfluoride material of the present invention. For dental compositions that include water, a preferred form of the oxyfluoride material to disperse in the composition is separated oxyfluoride material including sufficient water to form wet cakes or plastic solids. Oxyfluoride material in these forms is typically more convenient to disperse when the separated oxyfluoride material is never fully dried. For example, after precipitation and washing, wet oxyfluoride material separated by filtering, centrifuging, or filter pressing can include about 40 to 70% by weight water, and the wet oxyfluoride material can be added to dental compositions in this form.

Alternatively, if the washed precipitate is dried, a similarly dispersible wet cake or plastic mass can be formed by milling the dried precipitate in water, followed by separation by filtering, filter pressing, or centrifugation to form a dispersible wet oxyfluoride material.

After washing or milling in water, the oxyfluoride material can also be coated on a particle, coated on an aggregate of particles, infiltrated into a porous structure, or combinations thereof.

In another embodiment, the method includes providing a porous structure (e.g., porous particles, porous aggregates of particles, and combinations thereof); infiltrating a first liquid composition in the porous structure; and infiltrating a second liquid composition in the porous structure to provide a porous structure infiltrated with an acid-reactive oxyfluoride material. The first liquid composition includes a source of a trivalent metal and a source of an alkaline earth metal. The trivalent metal is preferably aluminum, lanthanum, or combinations thereof. More preferably the trivalent metal is aluminum. The second liquid composition includes a source of fluorine, and optionally, ammonium hydroxide, sodium hydroxide, potassium hydroxide, or combinations thereof. The second liquid optionally may further include a source of silicon. Preferably at least one of the first or second liquid compositions further includes water. Infiltrating the first liquid composition can be carried out before, during, or after infiltrating the second liquid composition.

Optionally the method further includes drying the porous structure infiltrated with the acid-reactive oxyfluoride material at a temperature of at most 350° C., more preferably at most 250° C., and most preferably at most 150° C.

Acids

Acids for use in the present invention can be inorganic or organic acids, and if organic can be-monomeric, oligomeric or polymeric (e.g., polyacids as described herein below). The acids may be polymerizable or non-polymerizable. If desired, a precursor to the acid such as an acid anhydride, acid halide (including inorganic acid halides such as Lewis acids, e.g., ferric chloride, and organic acid halides), or esters can be used in place of the acid itself, e.g., to generate the desired acid in situ. Suitable acids include mineral acids, carboxylic acids, sulfonic acids, alkylsulfonic acids, arylsulfonic acids, and phosphonic acids. The acid can be a liquid or a solid material.

Suitable inorganic acids include HBr, HCl, $HNO_3$, sulfuric acid, phosphoric acid, and phosphonic acid. Suitable organic acids include acetic acid, 2-chloropropionic acid, 2-acrylamido-2-methylpropane sulfonic acid, (meth)acrylic acid, benzenesulfonic acid, benzoic acid, bromoacetic acid, 10-camphorquinonesulfonic acid, 10-camphorsulfonic acid, chloroacetic acid, citraconic acid, citric acid, dibromoacetic acid, dichloroacetic acid, di-HEMA ester of 1,2,4,5 benzenetetracarboxylic acid, 2,4-dinitrophenol, formic acid, fumaric acid, 2-hydroxy-4-methoxybenzophenone-5-sulfonic acid, maleic acid, 2-naphthalene sulfonic acid, oxalic acid, p-nitrophenol, phenol, dibutyl phosphite, di-(2-ethylhexyl) phosphate, di-(2-ethylhexyl) phosphite, hydroxyethyl methacrylate monophosphate, glyceryl dimethacrylate phosphate, glyceryl-2-phosphate, glycerylphosphoric acid, methacryloxyethyl phosphate, pentaerythritol triacrylate monophosphate, pentaerythritol trimethacrylate monophosphate, pivalic acid, propionic acid, toluene sulfonic acid, tribromoacetic acid, trichloroacetic acid, trifluoroacetic acid, trifluoromethanesulfonic acid, and trihydroxybenzoic acid. Mixtures of such acids can be used if desired.

Polyacids

Dental compositions of the present invention may include at least one polyacid, which may be a non-curable or non-polymerizable polyacid, or a curable or polymerizable polyacid (e.g., a resin-modified polyacid). The polyacid need not be entirely water soluble, but it should be at least sufficiently water-miscible so that it does not undergo substantial sedimentation when combined with other aqueous components. Suitable polyacids are-listed in U.S. Pat. No. 4,209,434 (Wilson et al.), column 2, line 62, to column 3, line 6. The polyacid should have a molecular weight sufficient to provide good storage, handling, and mixing properties. A preferred weight average molecular weight is 5,000 to 100,000, evaluated against a polystyrene standard using gel permeation chromatography.

In one embodiment, the polyacid is a curable or polymerizable resin. That is, it contains at least one ethylenically unsaturated group. Suitable ethylenically unsaturated polyacids are described in U.S. Pat. No. 4,872,936 (Engelbrecht), e.g., at columns 3 and 4, and EP 323 120 B1 (Mitra), e.g., at page 3, line 55 to page 5, line 8. Preferably, the numbers of acidic groups and ethylenically unsaturated groups are adjusted to provide an appropriate balance of properties in the dental composition. Polyacids in which 10% to 30% of the acidic groups have been replaced with ethylenically unsaturated groups are preferred.

In other embodiments, the polyacid is hardenable in the presence of, for example, an acid-reactive filler and water, but does not contain ethylenically unsaturated groups. That is, it is an oligomer or polymer of an unsaturated acid. Preferably, the unsaturated acid is an oxyacid (i.e., an oxygen containing acid) of carbon, sulfur, phosphorous, or boron. More preferably, it is an oxyacid of carbon. Such polyacids include, for example, polyalkenoic acids such as homopolymers and copolymers of unsaturated mono-, di-, or tricarboxylic acids. Preferred polyalkenoic acids can be prepared by the homopolymerization and copolymerization of unsaturated aliphatic carboxylic acids, e.g., acrylic acid, 2-choloracrylic acid, 3-choloracrylic acid, 2-bromoacrylic acid, 3-bromoacrylic acid, methacrylic acid, itaconic acid, maleic acid, glutaconic acid, aconitic acid, citraconic acid, mesaconic acid, fumaric acid, and tiglic acid. Suitable monomers that can be copolymerized with the unsaturated aliphatic carboxylic acids include, for example, unsaturated aliphatic compounds such as acrylamide, acrylonitrile, vinyl chloride, allyl chloride, vinyl acetate, and 2-hydroxyethyl methacrylate. Ter- and higher polymers may be used if desired. Particularly preferred are the homopolymers and copolymers of acrylic acid. The polyalkenoic acid should be substantially free of unpolymerized monomers.

Ethylenically Unsaturated Compounds with Acid Functionality

Dental compositions of the present invention may include at least one ethylenically unsaturated compound with acid functionality.

As used herein, ethylenically unsaturated compounds with acid functionality is meant to include monomers, oligomers, and polymers having ethylenic unsaturation and acid and/or acid-precursor functionality. Acid-precursor functionalities include, for example, anhydrides, acid halides, and pyrophosphates. Preferably, the unsaturated acid is an oxyacid (i.e., an oxygen containing acid) of carbon, sulfur, phosphorous, or boron.

Ethylenically unsaturated compounds with acid functionality include, for example, α,β-unsaturated acidic compounds such as glycerol phosphate monomethacrylates, glycerol phosphate dimethacrylates, hydroxyethyl methacrylate phosphates, citric acid di- or tri-methacrylates, poly(meth)acrylated oligomaleic acid, poly(meth)acrylated polymaleic acid, poly(meth)acrylated poly(meth)acrylic acid, poly(meth)acrylated polycarboxyl-polyphosphonic acid, poly(meth)acrylated polychlorophosphoric acid, poly (meth)acrylated polysulfonate, poly(meth)acrylated polyboric acid, and the like, may be used as components in the hardenable resin system. Certain preferred compositions of the present invention include an ethylenically unsaturated compound with acid functionality having at least one P—OH moiety.

Certain of these compounds are obtained, for example, as reaction products between isocyanatoalkyl (meth)acrylates and carboxylic acids. Additional compounds of this type having both acid-functional and ethylenically unsaturated components are described in U.S. Pat. No. 4,872,936 (Engelbrecht) and U.S. Pat. No. 5,130,347 (Mitra). A wide variety of such compounds containing both the ethylenically unsaturated and acid moieties can be used. Mixtures of such compounds can be used if desired.

Additional ethylenically unsaturated compounds with acid functionality include, for example, polymerizable bis-phosphonic acids as disclosed for example, in U.S. application Ser. No. 10/729,497, filed Dec. 5, 2003; AA:ITA:IEM (copolymer of acrylic acid:itaconic acid with pendent methacrylate made by reacting AA:ITA copolymer with sufficient 2-isocyanatoethyl methacrylate to convert a portion of the acid groups of the copolymer to pendent methacrylate groups as described, for example, in Example 11 of U.S. Pat. No. 5,130,347 (Mitra)); and those recited in U.S. Pat. No. 4,259,075 (Yamauchi et al.), U.S. Pat. No. 4,499,251 (Omura et al.), U.S. Pat. No. 4,537,940 (Omura et al.), U.S. Pat. No. 4,539,382 (Omura et al.), U.S. Pat. No. 5,530,038 (Yamamoto et al.), U.S. Pat. No. 6,458,868 (Okada et al.), and European Pat. Application Publication Nos. EP 712,622 (Tokuyama Corp.) and EP 1,051,961 (Kuraray Co., Ltd.).

Preferably, the compositions of the present invention include at least 1% by weight, more preferably at least 3% by weight, and most preferably at least 5% by weight ethylenically unsaturated compounds with acid functionality, based on the total weight of the unfilled composition. Preferably, compositions of the present invention include at most 80% by weight, more preferably at most 70% by weight, and most preferably at most 60% by weight ethylenically unsaturated compounds with acid functionality, based on the total weight of the unfilled composition.

Hardenable Resins

Dental compositions of the present invention can include a hardenable resin. These resins preferably are generally thermosetting materials capable of being hardened to form a polymer network including, for example, acrylate-functional materials, methacrylate-functional materials, epoxy-functional materials, vinyl-functional materials, and mixtures thereof. Preferably, the hardenable resin is made from one or more matrix-forming oligomer, monomer, polymer, or blend thereof.

In a preferred embodiment where the dental composition disclosed in the present application is a dental composite, polymerizable materials suitable for use include hardenable organic materials having sufficient strength, hydrolytic stability, and non-toxicity to render them suitable for use in the oral environment. Examples of such materials include acrylates, methacrylates, urethanes, carbamoylisocyanurates, epoxies, and mixtures and derivatives thereof.

One class of preferred hardenable materials includes materials having free radically active functional groups. Examples of such materials include monomers having one or more ethylenically unsaturated group, oligomers having one or more ethylenically unsaturated group, polymers having one or more ethylenically unsaturated group, and combinations thereof.

Free Radically Active Materials. In the class of hardenable resins having free radically active functional groups, suitable materials for use in the invention contain at least one ethylenically unsaturated bond, and are capable of undergoing addition polymerization. Such free radically polymerizable compounds include, for example, mono-, di- or poly-(meth)acrylates (i.e., acrylates and methacrylates) such as, methyl (meth)acrylate, ethyl acrylate, isopropyl methacrylate, n-hexyl acrylate, stearyl acrylate, allyl acrylate, glycerol triacrylate, ethyleneglycol diacrylate, diethyleneglycol diacrylate, triethyleneglycol dimethacrylate, 1,3-propanediol di(meth)acrylate, trimethylolpropane triacrylate, 1,2,4-butanetriol trimethacrylate, 1,4-cyclohexanediol diacrylate, pentaerythritol tetra(meth)acrylate, sorbitol hexacrylate, tetrahydrofurfuryl (meth)acrylate, bis[1-(2-acryloxy)]-p-ethoxyphenyldimethylmethane, bis[1-(3-acryloxy-2-hydroxy)]-p-propoxyphenyldimethylmethane, ethoxylated bisphenol A di(meth)acrylate, and trishydroxyethyl-isocyanurate trimethacrylate; (meth)acrylamides (i.e., acrylamides and methacrylamides) such as (meth)acrylamide, methylene bis-(meth)acrylamide, and diacetone (meth)acrylamide; urethane (meth)acrylates; the bis-(meth)acrylates of polyethylene glycols (preferably of molecular weight 200–500); copolymerizable mixtures of acrylated monomers such as those in U.S. Pat. No. 4,652, 274 (Boettcher et al.); acrylated oligomers such as those of U.S. Pat. No. 4,642,126 (Zador et al.); and vinyl compounds such as styrene, diallyl phthalate, divinyl succinate, divinyl adipate and divinyl phthalate. Other suitable free radically polymerizable compounds include siloxane-functional (meth)acrylates as disclosed, for example, in WO-00/38619 (Guggenberger et al.), WO-01/92271 (Weinmann et al.), WO-01/07444 (Guggenberger et al.), WO-00/42092 (Guggenberger et al.) and fluoropolymer-functional (meth)acrylates as disclosed, for example, in U.S. Pat. No. 5,076,844 (Fock et al.), U.S. Pat. No. 4,356,296 (Griffith et al.), EP-0 373 384 (Wagenknecht et al.), EP-0 201 031 (Reiners et al.), and EP-0 201 778 (Reiners et al.). Mixtures of two or more free radically polymerizable compounds can be used if desired.

The polymerizable component may also contain hydroxyl groups and free radically active functional groups in a single molecule. Examples of such materials include hydroxyalkyl (meth)acrylates, such as 2-hydroxyethyl (meth)acrylate and 2-hydroxypropyl (meth)acrylate; glycerol mono- or di-(meth)acrylate; trimethylolpropane mono- or di-(meth)acrylate; pentaerythritol mono-, di-, and tri-(meth)acrylate; sorbitol mono-, di-, tri-, tetra-, or penta-(meth)acrylate; and 2,2-bis[4-(2-hydroxy-3-methacryloxypropoxy)phenyl]propane (bisGMA). Suitable ethylenically unsaturated compounds are also available from a wide variety of commercial sources, such as Sigma-Aldrich, St. Louis, Mo. and Rohm Tech, Inc., Malden, Mass. Mixtures of ethylenically unsaturated compounds can be used if desired.

Free Radical Initiation Systems. For free radical polymerization (e.g., hardening), an initiation system can be selected from systems that initiate polymerization via radiation, heat, or redox/auto-cure chemical reaction. A class of initiators capable of initiating polymerization of free radically active functional groups includes free radical-generating photoinitiators, optionally combined with a photosensitizer or accelerator. Such initiators typically can be capable of generating free radicals for addition polymerization upon exposure to light energy having a wavelength between 200 and 800 nm.

Suitable photoinitiators (i.e., photoinitiator systems that include one or more compounds) for polymerizing free radically photopolymerizable compositions include binary and ternary systems. Typical ternary photoinitiator systems include an iodonium salt, a photosensitizer, and an electron donor compound as described in U.S. Pat. No. 5,545,676 (Palazzotto et al.). Preferred iodonium salts are the diaryl iodonium salts, e.g., diphenyliodonium chloride, diphenyliodonium hexafluorophosphate, and diphenyliodonium tetrafluoroborate. Preferred photosensitizers are monoketones and diketones that absorb some light within a range of 400 nm to 520 nm (preferably, 450 nm to 500 nm). More preferred compounds are alpha diketones that have some light absorption within a range of 400 nm to 520 nm (even more preferably, 450 to 500 nm). Preferred compounds are camphorquinone, benzil, furil, 3,3,6,6-tetramethylcyclohexanedione, phenanthraquinone and other cyclic alpha diketones. Most preferred is camphorquinone. Preferred electron donor compounds include substituted amines, e.g., ethyl dimethylaminobenzoate. Other suitable ternary photoinitiator systems useful for photopolymerizing cationically polymerizable resins are described, for example, in U.S. patent Publication No. 2003/0166737 (Dede et al.).

Other suitable photoinitiators for polymerizing free radically photopolymerizable compositions include the class of phosphine oxides that typically have a functional wavelength range of 380 nm to 1200 nm. Preferred phosphine oxide free radical initiators with a functional wavelength range of 380 nm to 450 nm are acyl and bisacyl phosphine oxides such as those described in U.S. Pat. No. 4,298,738 (Lechtken et al.), U.S. Pat. No. 4,324,744 (Lechtken et al.), U.S. Pat. No. 4,385,109 (Lechtken et al.), U.S. Pat. No. 4,710,523 (Lechtken et al.), and U.S. Pat. No. 4,737,593 (Ellrich et al.), U.S. Pat. No. 6,251,963 (Kohler et al.); and EP Application No. 0 173 567 A2 (Ying). P Commercially available phosphine oxide photoinitiators capable of free-radical initiation when irradiated at wavelength ranges of greater than 380 nm to 450 nm include, for example, bis(2,4,6-trimethylbenzoyl)phenyl phosphine oxide available under the trade designation IRGACURE 819 from Ciba Specialty Chemicals, Tarrytown, N.Y.; bis(2,6-dimethoxybenzoyl)-(2,4,4-trimethylpentyl)phosphine oxide available under the trade designation CGI 403 from Ciba Specialty Chemicals; a 25:75 mixture, by weight, of bis(2,6-dimethoxybenzoyl)-2,4,4-trimethylpentyl phosphine oxide and 2-hydroxy-2-methyl-1-phenylpropan-1-one available under the trade designation IRGACURE 1700 from Ciba Specialty Chemicals; a 1:1 mixture, by weight, of bis(2,4,6-trimethylbenzoyl)phenyl phosphine oxide and 2-hydroxy-2-methyl-1-phenylpropane-1-one available under the trade designation DAROCUR 4265 from Ciba Specialty Chemicals; and ethyl 2,4,6-trimethylbenzylphenyl phosphinate available under the trade designation LUCIRIN LR8893X from BASF Corp., Charlotte, N.C.

Typically, the phosphine oxide initiator is present in the photopolymerizable composition in catalytically effective amounts, such as from 0.1% by weight to 5% by weight, based on the total weight of the composition.

Tertiary amine reducing agents may be used in combination with an acylphosphine oxide. Illustrative tertiary amines useful in the invention include ethyl 4-(N,N-dimethylamino) benzoate and N,N-dimethylaminoethyl methacrylate. When present, the amine reducing agent is present in the photopolymerizable composition in an amount from 0.1% by weight to 5% by weight, based on the total weight of the composition. Useful amounts of other initiators are well known to those of skill in the art.

Another free-radical initiator system that can alternatively be used in the dental materials of the invention includes the class of ionic dye-counterion complex initiators including a borate anion and a complementary cationic dye. Borate salt photoinitiators are described, for example, in U. S. Pat. No. 4,772,530 (Gottschalk et al.), U.S. Pat. No. 4,954,414 (Adair et al.), U.S. Pat. No. 4,874,450 (Gottschalk), U.S. Pat. No. 5,055,372 (Shanklin et al.), and U.S. Pat. No. 5,057,393 (Shanklin et al.).

The hardenable resins of the present invention can include redox cure systems that include a polymerizable component (e.g., an ethylenically unsaturated polymerizable component) and redox agents that include an oxidizing agent and a reducing agent. Suitable polymerizable components and redox agents that are useful in the present invention are described in U.S. patent Publication No. 2003/0166740 (Mitra et al.) and U.S. patent Publication No. 2003/0195273 (Mitra et al.).

The reducing and oxidizing agents should react with or otherwise cooperate with one another to produce free-radicals capable of initiating polymerization of the resin system (e.g., the ethylenically unsaturated component). This type of cure is a dark reaction, that is, it is not dependent on the presence of light and can proceed in the absence of light. The reducing and oxidizing agents are preferably sufficiently shelf-stable and free of undesirable colorization to permit their storage and use under typical dental conditions. They should be sufficiently miscible with the resin system (and preferably water-soluble) to permit ready dissolution in (and discourage separation from) the other components of the polymerizable composition.

Useful reducing agents include, for example, ascorbic acid, ascorbic acid derivatives, and metal complexed ascorbic acid compounds as described in U.S. Pat. No. 5,501,727 (Wang et al.); amines, especially tertiary amines, such as 4-tert-butyl dimethylaniline; aromatic sulfinic salts, such as p-toluenesulfinic salts and benzenesulfinic salts; thioureas, such as 1-ethyl-2-thiourea, tetraethyl thiourea, tetramethyl thiourea, 1,1-dibutyl thiourea, and 1,3-dibutyl thiourea; and mixtures thereof. Other secondary reducing agents may include cobalt (II) chloride, ferrous chloride, ferrous sulfate, hydrazine, hydroxylamine (depending on the choice of oxidizing agent), salts of a dithionite or sulfite anion, and combinations thereof. Preferably, the reducing agent is an amine.

Suitable oxidizing agents will also be familiar to those skilled in the art, and include, for example, persulfuric acid and salts thereof, such as sodium, potassium, ammonium, cesium, and alkyl ammonium salts. Additional oxidizing agents include, for example, peroxides such as benzoyl peroxides, hydroperoxides such as cumyl hydroperoxide, t-butyl hydroperoxide, and amyl hydroperoxide, as well as salts of transition metals such as cobalt (III) chloride and ferric chloride, cerium (IV) sulfate, perboric acid and salts thereof, permanganic acid and salts thereof, perphosphoric acid and salts thereof, and combinations thereof.

It may be desirable to use more than one oxidizing agent or more than one reducing agent. Small quantities of transition metal compounds may also be added to accelerate the rate of redox cure. In some embodiments it may be preferred to include a secondary ionic salt to enhance the stability of the hardenable composition as described, for example, in U.S. patent Publication No. 2003/0195273 (Mitra et al.).

The reducing and oxidizing agents are present in amounts sufficient to permit an adequate free-radical reaction rate. This can be evaluated by combining all of the ingredients of the hardenable composition except for the filler, and observing whether or not a hardened mass is obtained.

Preferably, the reducing agent is present in an amount of at least 0.01% by weight, and more preferably at least 0.1% by weight, based on the total weight (including water) of the components of the hardenable composition. Preferably, the reducing agent is present in an amount of no greater than 10% by weight, and more preferably no greater than 5% by weight, based on the total weight (including water) of the components of the polymerizable composition.

Preferably, the oxidizing agent is present in an amount of at least 0.01% by weight, and more preferably at least 0.10% by weight, based on the total weight (including water) of the components of the polymerizable composition. Preferably, the oxidizing agent is present in an amount of no greater than 10% by weight, and more preferably no greater than 5% by weight, based on the total weight (including water) of the components of the hardenable composition.

The reducing or oxidizing agents can be microencapsulated as described, for example, in U.S. Pat. No. 5,154,762 (Mitra et al.). This will generally enhance shelf stability of the polymerizable composition, and if necessary permit packaging the reducing and oxidizing agents together. For example, through appropriate selection of an encapsulant, the oxidizing and reducing agents can be combined with an acid-functional component and optional filler and kept in a storage-stable state. Likewise, through appropriate selection of a water-insoluble encapsulant, the reducing and oxidizing agents can be combined with an FAS glass and water and maintained in a storage-stable state.

In a further alternative, heat may be used to initiate the hardening, or polymerization, of free radically active groups. Examples of heat sources suitable for the dental materials of the invention include inductive, convective, and radiant. Thermal sources should be capable of generating temperatures of at least 40° C. and at most 150° C. under normal conditions or at elevated pressure. This procedure is preferred for initiating polymerization of materials occurring outside of the oral environment.

Yet another alternative class of initiators capable of initiating polymerization of free radically active functional groups in the hardenable resin are those that include free radical-generating thermal initiators. Examples include peroxides (e.g., benzoyl peroxide and lauryl peroxide) and azo compounds (e.g., 2,2-azobis-isobutyronitrile (AIBN)).

Photoinitiator compounds are preferably provided in dental compositions disclosed in the present application in an amount effective to initiate or enhance the rate of cure or hardening of the resin system. Useful photopolymerizable compositions are prepared by simply admixing, under safe light conditions, the components as described above. Suitable inert solvents may be used, if desired, when preparing this mixture. Any solvent that does not react appreciably with the components of the inventive compositions may be used. Examples of suitable solvents include, for example, acetone, dichloromethane, and acetonitrile.

Other Fillers

In addition to the dental filler that includes an acid-reactive oxyfluoride material, the compositions of the present invention can also optionally contain one or more other fillers. Such fillers may be selected from one or more of a wide variety of materials suitable for incorporation in compositions used for dental applications, such as fillers currently used in dental restorative compositions, and the like.

The other filler is preferably finely divided. The filler can have a unimodial or polymodial (e.g., bimodal) particle size distribution. Preferably, the maximum particle size (the largest dimension of a particle, typically, the diameter) of the other filler is less than 5 micrometers, more preferably less than 0.5 micrometers, and most preferably less than 0.1 micrometers. Preferably, the average particle size of the filler is less than 0.1 micrometers, and more preferably less than 0.075 micrometer.

The other filler can be an inorganic material. It can also be a crosslinked organic material that is insoluble in the resin component of the composition, and is optionally filled with inorganic filler. The filler should in any event be nontoxic and suitable for use in the mouth. The filler can be radiopaque or radiolucent. The filler typically is substantially insoluble in water.

Examples of suitable inorganic fillers are naturally occurring or synthetic materials including, but not limited to: quartz; nitrides (e.g., silicon nitride); glasses derived from, for example, Zr, Sr, Ce, Sb, Sn, Ba, Zn, and Al; feldspar; borosilicate glass; kaolin; talc; titania; low Mohs hardness fillers such as those described in U.S. Pat. No. 4,695,251 (Randklev); and submicron silica particles (e.g., pyrogenic silicas such as those available under the trade designations AEROSIL, including "OX 50," "130," "150" and "200" silicas from Degussa AG, Hanau, Germany and CAB-O-SIL M5 silica from Cabot Corp., Tuscola, Ill.). Examples of suitable organic filler particles include filled or unfilled pulverized polycarbonates, polyepoxides, and the like.

Suitable non-acid-reactive filler particles are quartz, submicron silica, and non-vitreous microparticles of the type described in U.S. Pat. No. 4,503,169 (Randklev). Mixtures of these non-acid-reactive fillers are also contemplated, as well as combination fillers made from organic and inorganic materials.

The surface of the filler particles can also be treated with a coupling agent in order to enhance the bond between the filler and the resin. The use of suitable coupling agents include gamma-methacryloxypropyltrimethoxysilane, gamma-mercaptopropyltriethoxysilane, gamma-aminopropyltrimethoxysilane, and the like.

Other suitable fillers are disclosed in U.S. Pat. No. 6,387,981 (Zhang et al.) and U.S. Pat. No. 6,572,693 (Wu et al.) as well as International Publication Nos. WO 01/30305 (Zhang et al.), WO 01/30306 (Windisch et al.), WO 01/30307 (Zhang et al.), and WO 03/063804 (Wu et al.). Filler components described in these references include nanosized silica particles and metal oxides, such as the oxides of yttrium, strontium, barium, zirconium, hafnium, niobium, tantalum, tungsten, bismuth, molybdenum, tin, zinc, lanthanide elements (i.e. elements having atomic numbers ranging from 57 to 71, inclusive), and cerium and combinations thereof.

For some embodiments of the present invention that include other fillers (e.g., dental restorative compositions), the compositions preferably include at least 1% by weight, more preferably at least 2% by weight, and most preferably at least 5% by weight other filler, based on the total weight of the composition. For such embodiments, compositions of the present invention preferably include at most 40% by weight, more preferably at most 20% by weight, and most preferably at most 15% by weight other filler, based on the total weight of the composition.

For other embodiments of the present invention (e.g., wherein the composition is a dental restorative or an orthodontic adhesive, and where the other filler is the majority of the total filler in the composition), compositions of the present invention preferably include at least 40% by weight, more preferably at least 45% by weight, and most preferably at least 50% by weight other filler, based on the total weight of the composition. For such embodiments, compositions of the present invention preferably include at most 90% by weight, more preferably at most 80% by weight, even more preferably at most 70% by weight, and most preferably at most 50% by weight other filler, based on the total weight of the composition.

Other Additives

The inventive dental compositions may optionally include additives suitable for use in the oral environment including, for example, colorants, flavorants, anti-microbials, fragrances, stabilizers, viscosity modifiers, and inorganic and organic fluoride releasing materials (e.g. FAS glass and organic fluoride sources such as those described in U.S. Pat. No. 4,871,786 (Aasen et al.)). For example, suitable additives include agents that impart fluorescence and/or opalescence.

Incorporation of Fillers

Fillers disclosed in the present application may be incorporated in a hardenable resin and/or a polyacid by any suitable means to form a dental composition. Acid-reactive dental fillers may be added as a powder. Alternatively, the acid-reactive dental filler may be combined with another filler (e.g., an acid-reactive filler, a non acid-reactive filler, a nanosized filler) and/or optional additives to provide a material that can then be added as a powder to the hardenable resin or polyacid. Alternatively, the acid-reactive dental filler may be combined with liquid additives and added to the hardenable resin or polyacid as a dispersion. Further, wet acid-reactive dental fillers can be combined with a resin as described in the Examples herein.

Dental Compositions

In one embodiment, dental fillers of the present invention can be incorporated in a hardenable resin to provide useful dental compositions as described herein above. For some applications, the dental composition is preferably in the form of a paste. Dental compositions of the present invention can be chemically curable, heat curable, or light curable compositions. Light curable materials should have an appropriate initiator system. Chemically curable materials can be auto-cure (e.g. via redox initiators). Alternatively, the compositions can be hardened by a combination of auto- and light-cure. Dental compositions of the present invention can be single-part or multi-part dental compositions. Preferably, the compositions are shelf-stable compositions, that is, they have a room-temperature shelf-life stability of at least 1 year, and preferably at least 2 years.

In other embodiments, dental compositions disclosed in the present application include a dental filler that includes an acid-reactive oxyfluoride material disposed in the resin. The amount of filler used depends on the type of composition and on the desired properties.

In further embodiments, dental fillers of the present invention are useful in ionomer type compositions, such as conventional glass ionomers, which typically include a polyacid, an acid-reactive filler, and water; and resin modified glass ionomers, which typically include a polyacid, an acid-reactive filler, a hardenable resin (i.e. a polymerizable component), and water. Dental fillers of the present invention can be used as partial or complete replacements for conventional FAS glass fillers, which are typically used as acid-reactive fillers.

Preferably dental fillers of the present invention have a high surface area, allowing them to be used in relatively small amounts, but still providing fluoride release and ionomer curing comparable to higher loadings of conventional FAS glasses. The use of relatively small amounts of dental fillers of the present invention allows for the formulation of ionomer and/or fluoride releasing dental compositions including larger amounts of additional desired fillers, such as radiopaque fillers, indexed matched fillers, and/or nanofillers. In some embodiments, such compositions can have less than 15% by weight of dental fillers of the present invention, or less than 10% in other embodiments, or less than 5% in still other embodiments. In some embodiments, the dental fillers in such compositions can provide a filler surface area of at least 2 square meters, in other embodiments at least 5 square meters, and in still other embodiments at least 10 square meters, per gram of dental composition, despite the relatively low loadings.

Dental compositions of the present invention can optionally include, in addition to the dental filler of the present invention, relatively large amounts of additional fillers. In some embodiments, the dental composition includes at most 10% by weight of dental fillers of the present invention, but also includes at least 40% by weight additional fillers, in other embodiments at least 50% by weight, and in still other embodiments at least 60% by weight, based on the total weight of the dental composition.

By using either relatively small amounts of dental fillers of the present invention (e.g., nanostructured oxyfluoride material, and particularly, primarily nanosized filler of the present invention), and additional nanosized fillers, dental compositions can be formulated that have filler systems including primarily or essentially completely nanofillers. In some embodiments, the total filler content includes at least 75% nanofillers, and in other embodiments at least 90% nanofillers.

In further embodiments, dental compositions include higher loadings of dental fillers of the present invention. Preferably, the dental compositions include at most 75% by weight, and more preferably at most 70% by weight of dental fillers of the present invention, based on the total weight of the dental composition.

In still further embodiments, dental compositions preferably include at least 2% by weight, and more preferably at least 5% by weight of dental fillers of the present invention, based on the total weight of the dental composition.

The dental compositions disclosed in the present application can be used, for example, as dental adhesives, artificial crowns, anterior or posterior fillings, cavity liners, cements, coatings, mill blanks, orthodontic devices, orthodontic adhesives, restoratives, prostheses, and sealants. In a preferred aspect, the dental composition is a dental restorative. The restoratives of the invention can be placed directly in the mouth and cured (hardened) in situ, or alternatively, may be fabricated into a prosthesis outside the mouth and subsequently adhered in place inside the mouth.

Preferably, the present invention provides dental compositions that are capable of being hardened to provide a balance of desirable properties as detailed below (e.g., a high diametral tensile strength, a high compressive strength, and a high adhesion value) while retaining excellent handling and rheological properties (e.g., no substantial settling after 5 days of storage at 25° C.). Preferably, the dental composition is non-sticky when handled using well known procedures by one of skill in the art.

Multi-Part Dental Compositions

In one embodiment, the invention provides a multi-part (e.g., two or more part) dental composition. Each part may independently be, for example, a powder, a liquid, a gel, or a paste. Such multi-part dental systems include, for example, compositions that include an acid-reactive filler and a hardenable resin, and iononmeric compositions that include an acid-reactive filer, polyacid, and optional hardenable resin (i.e., a polymerizable component). As described herein, the acid-reactive fillers of the present invention can replace all or a portion of an FAS glass filler that are typically included in such compositions.

For example, a two-part ionomer system can include a part A, which includes an acid-reactive filler, and a part B, which includes a polyacid. Part A and Part B can be combined to form a mixed ionomer composition. The viscosity of part A is typically greater than 50,000 centipoise (cps), preferably between 150,000 to 300,000 cps when measured at or near room temperature (nominally 25° C.) using a Brookfield viscometer using a T-D spindle with a conversion factor equal to 32,000. Typically, a dental practitioner mixes the two parts immediately prior to use. As the two parts are mixed, an acid-base hardening reaction begins. Preferably the mixture has a working time, as defined in U.S. Pat. No. 5,925,715 (Mitra), of at least 30 seconds, and more preferably at least 60 seconds. Optionally, if a polymerizable component is present, subsequent hardening of the polymerizable component can be facilitated by curing agents and/or by light. Each component used to formulate parts A and B is discussed in detail herein. Certain components such as polymerizable components and initiator components may reside in either part A, part B, or both part A and part B as further explained below. The polyacid and the polymerizable component may be the same or different.

In one embodiment, the dental fillers disclosed in the present invention may be used in a part A of an ionomer composition. Part A may optionally include a polymerizable component. When used in part A of an ionomer composition, the composition preferably includes at least 5% by weight, more preferably at least 10% by weight, and most preferably at least 15% by weight of the dental filler of the present invention, based on the total weight of part A of the composition. When used in a part A of an ionomer composition, the composition preferably includes at most 85% by weight, more preferably at most 82% by weight, and most preferably at most 80% by weight of the dental filler of the present invention, based on the total weight of part A of the composition.

The amount of polyacid in the dental composition, whether as part of a hardenable polymerizable resin or a non-polymerizable hardenable polyacid, should be sufficient to provide a desired balance of properties. Part B preferably includes at least 5% by weight of the polyacid and more preferably at least 10% by weight of the polyacid, based on the total weight of part B. Part B preferably includes at most 70% by weight of the polyacid and more preferably at most 60% by weight of the polyacid, based on the total weight of part B.

Parts A and/or B can optionally contain water, which can be present in the product as sold or added by the dental practitioner just prior to use. The water can be distilled, deionized (DI), or tap water, with deionized water being preferred. Just prior to use, the total dental composition preferably includes at least 1% by weight water, more preferably at least 3% by weight water, and most preferably at least 5% by weight water. Just prior to use, the total dental composition preferably includes at most 35% by weight water, and more preferably at most 25% by weight water. In general, the amount of water used should be sufficient to provide adequate handling and mixing properties for the dental composition and to permit the transport of ions in the acid-reactive dental filler-polyacid reaction. When water and filler of the present invention are both included in part A, an aqueous paste or stiff clay-like form of the filler can be used in the formulation of part A.

Optionally, multi-part dental systems of the present invention can include additional non acid-reactive or acid-reactive fillers including, for example, nanofillers.

In some implementations of the invention, at least 90% by weight of the non acid-reactive dental filler is in the form of nanoparticles.

In some embodiments, two-part dental compositions of the present invention can be provided in a dual barrel syringe having a first barrel and a second barrel, wherein the part A resides in the first barrel and the part B resides in the second barrel. In other embodiments, two-part dental compositions of the present invention can be provided in a unit-dose capsule. In some embodiments, each part of a multi-part dental system can be mixed together using a static mixer.

Hardened Dental Compositions

Dental compositions disclosed in the present application include a dental filler of the present invention disposed in a hardenable resin (e.g., a polymerizable component), have especially desirable handling (e.g., rheological) properties in an unhardened state and high strength in a hardened state.

Strength can be characterized by mechanical measurements such as compressive strength (CS) and diametral tensile strength (DTS). High compressive strength in a dental material is advantageous due to the forces exerted by mastication on dental repairs, replacements and restorations. Diametral tensile strength indicates the dental material's ability to withstand compression forces that introduce a tensile stress in the material. Tests for each strength measurement are set out below in the Examples.

The dental compositions disclosed in the present application, when hardened, preferably have a compressive strength of at least 60 MPa; more preferably, a compressive strength of at least 80 MPa; and most preferably, a compressive strength of at least 90 MPa. Hardened dental compositions of the invention preferably have a diametral tensile strength of at least 10 MPa; more preferably at least 15 MPa; and most preferably at least 20 MPa.

Dental Articles

The dental compositions of the present invention may be hardened to form, for example, dental articles (e.g., crowns, fillings, mill blanks, and prostheses) and orthodontic devices. In a preferred method of using dental compositions including a hardenable resin and dental fillers of the present invention, the composition may be placed near or on a tooth surface, followed by a manipulation by the practitioner or laboratory to change the topography of the composition, followed by hardening of the composition. These steps can be followed sequentially or in a different order. For example, in a preferred embodiment where the dental composition is a mill blank or a prosthesis, the hardening step is generally completed prior to changing the topography of the composition. Changing the topography of the composition can be accomplished in various ways including, for example, carving or manual manipulation using hand held instruments, or by machine or computer aided apparatus (e.g., a CAD/CAM milling machine) in the case of prostheses and mill blanks. Optionally, a finishing step can be performed to polish, finish, or apply a coating on the dental article.

Objects and advantages of this invention are further illustrated by the following examples, but the particular materials and amounts thereof recited in these examples, as well as other conditions and details, should not be construed to unduly limit this invention. Unless otherwise indicated, all parts and percentages are on a weight basis, all water is deionized water, and all molecular weights are weight average molecular weight.

EXAMPLES

Test Methods

Surface Area Determination

Surface area is related to the "primary particle size" of precipitated powders. The primary particle size refers to the small, individually nucleated particles that form during precipitation. The primary particles can agglomerate to form larger particles, and might or might not be individually dispersible. The surface area (S) of uniform, spherical dense primary particles, and agglomerates or structures made from them, is approximately 3 m/$\rho$r, where m is mass, r is the primary particle radius, $\rho$ is the density, and S/m is the specific surface area. Therefore r=3 m/$\rho$S.

Filler powder specific surface area (surface area per unit weight) was determined by using a Micromeritics Gemini Surface Area Analyzer and a Micromeritics Flow Prep outgassing unit (Micromeritics, Norcross, Ga.). A powder sample was weighed out then placed into a glass sample tube. The weights of both a powder sample and a glass sample tube and stopper were weighed out and recorded. The powder sample was placed into the glass sample tube, weighed, and recorded. The nitrogen flow to the probe in the outgassing unit was turned on and then gently placed to the bottom on the glass sample tube. The stopper was loosely inserted to the top of the glass sample tube and the tube was placed into the heating zone of the prep outgassing unit. The sample was then allowed to outgas for 1 hour at 250° C. The tube was then removed from the heating zone and placed in the cooling rack to cool for 5 minutes. The stopper and probe were then removed from the glass tube. The stopper was then immediately replaced to the top of the glass tube. The tube plus stopper was then weighed and the weight subtracted from the initial weight of the glass tube and stopper only. Next-the glass tube with outgassed powder inside was placed up into the surface area analyzer. A Dewar flask was then filled with liquid nitrogen and placed into the surface area analyzer. The vacuum pump attached to the analyzer was then turned on. The Gemini control box was then used to input the powder weight, saturation pressure, evacuation rate, date, and time. The analysis was then started by pressing the enter button. Several cycles of analysis occurred and the surface area measurement was calculated by the program.

Particle Size Determination

Average Particle Size by Particle Size Analyzer: Particle size (including cluster size) distribution (based on volume percent) was determined using a Coulter LS 230 Particle Size Analyzer (Coulter Corporation, Hialeah, Fla.). The Analyzer was equipped with a Polarization Intensity Differential Scanning (PIDS) software. A 300-mg sample of filler was added into a glass vial with enough MICRO-90 surfactant (Cole-Parmer, Vernon Hills, N.Y.) to wet all the filler. A 30-ml aliquot of Calgon Solution (made by thoroughly mixing 0.20 g sodium fluoride, 4.00 g sodium pyrophosphate, 40.00 g sodium hexametaphosphate, 8.00 g MICRO-90 surfactant, and 3948 ml of DI water) was added and the resulting mixture shaken for 15 minutes and sonicated by a probe sonicator (Model W-225 Sonicator, Heat Systems-Ultrasonics, Farmingdale, N.Y.) for 6 min at an output control knob setting of 9. Particle analysis was conducted using Coulter LS 230 Particle Characterization Software Version 3.01. Testing conditions were 90 seconds for Run Length, 0 seconds for Wait Length, and the test sample was added dropwise into the sample orifice until the PIDS reading was between 45% and 55%. Three sets of data per sample were averaged to obtain the average particle or cluster size.

Average Particle Size by TEM (Transmission Electron Microscopy): Samples approximately 80-nm thick were placed on 200-mesh copper grids with carbon stabilized formvar substrates (SPI Supplies, a division of Structure Probe, Inc., West Chester, Pa.). A transmission electron micrograph (TEM) was taken using a JEOL 200CX Instrument (JEOL, Ltd. of Akishima, Japan and sold by JEOL USA, Inc.) at 200 Kv. A population size of about 50–100 particles was measured and an average particle size was determined.

Fluoride Release Test Method

The amount of fluoride released from a filler powder sample was determined by the following procedure. Disc-shaped (1-mm thick×20-mm diameter) paste samples were cured by exposing them to illumination from a VISILUX 2 curing light (3M Company, St. Paul, Minn.) for 60 seconds. The hardened disc was then weighed and added to 25 ml of DI water in a plastic vial. The vial was then placed in a 37° C. oven for 24 hours. The vial was then taken out of the oven and 10 ml of the water solution was added to 10 ml of TISAB (Total Ionic Strength Adjustment Buffer containing DI water, sodium acetate, sodium chloride, acetic acid, and CDTA (1,2-cyclohexane diaminetetraacetic acid) (Thermo Orion, Beverly, Mass.). A magnetic stir bar was added and the solution was mixed on a stir plate. The Orion Fluoride Combination electrode model 96-09 was then standardized using Orion IonPlus standard solutions (Orion, Boston, Mass.) of 1, 2, 5, 10, 50, and 100 ppm. Once calibrated, the electrode was placed in the stirring water/TISAB solution and the value in ppm was measured. Fluoride release was calculated considering the total amount of water initially used for a disc sample (25 ml) and the individual weight of the disc sample. This calculation resulted in units of $\mu$g F/g and represented the average of three replicates.

Total Fluoride Content Test Method

The total amount of fluoride present in a filler powder sample was determined by the following procedure. A filler powder sample was analyzed for fluoride release as described in the above Fluoride Release Test Method, except that the sample was fully dissolved in an acetic acid solution in order to release all of the fluoride present in the sample. The results were reported as weight-percent fluoride and represented the average of three replicates.

Curing Efficiency Test Method

The Curing Efficiency of a filler powder sample was determined by the following procedure. A Test Resin was prepared by premixing and homogenizing a combination of VBCP (43 parts), HEMA (22.6 parts), and water (34.4 parts). A filler powder sample (variable amounts) was added to the Test Resin (0.5 g) and the resulting mixture was mixed with a spatula on a mixing pad until homogeneous and then formed into a disc-shaped sample approximately 2 cm in diameter and 1 mm thick using a TEFLON mold. The resulting disc sample was periodically examined and graded for extent of cure using the following scale:

0—no change from as mixed condition
1—increased viscosity—still liquid or flowable and paste-like
2—partially solid, sticky
3—solid, but flexible and tacky
4—fully solid, slight flexibility
5—fully cured, brittle The numbers (0–5) were recorded to represent a qualitative extent of cure at various total cure times.

Adhesion to Enamel or Dentin Test Method

Adhesive strength to enamel or dentin for a given test sample was evaluated by the following procedure.

Preparation of Teeth. For each test sample, five bovine teeth of similar age and appearance were partially embedded in circular acrylic discs. The exposed portion of each tooth was ground flat and parallel to the acrylic disc using Grade 120 silicon carbide paper-backed abrasive mounted on a lapidary wheel, in order to expose the dentin or enamel. During this and subsequent grinding and polishing steps, the teeth were continuously rinsed with water. Further grinding and polishing of the teeth was carried out by mounting Grade 600 silicon carbide paper-backed abrasive on the lapidary wheel. The polished teeth were stored in deionized water and used for testing within 2 hours after polishing. The polished teeth were removed from the water and blotted dry.

Application to Teeth: Previously made molds of 2-mm thick TEFLON sheeting with a 5-mm diameter hole were lined with a plastic ring so that the test sample (once cured) would release from them. The molds were clipped to the blotted dry teeth, prepared by grinding/polishing previously. Paste A and Paste B test samples were weighed out and mixed together for 25 seconds to afford a mixed paste test sample that was then spatulated into the mold. Slight pressure was applied to the mixed paste test sample to insure that it was at the mold/tooth intersection. After all the molds were filled, the samples were exposed to radiation from a XL 3000 dental curing light (3M Company) for 60 seconds. The samples were then placed in a humidity chamber set at 97% relative humidity and 37° C. for 15 minutes. The samples were then taken out of the chamber and the clips were removed from the assembly. The resultant tooth with the mold still attached was then placed into 37° C. deionized water for 24 hours in an over set at 37° C.

Adhesive Bond Strength Testing. The adhesive strength of a cured test sample was evaluated by mounting the assembly (described above) in a holder clamped in the jaws of an Instron testing machine (Instron 4505, Instron Corp. Canton, Mass.) with the polished tooth surface oriented parallel to the direction of pull. The sample molds were taken off prior to the testing. A loop of orthodontic wire (0.44-mm diameter) was placed around the button sample adjacent to the polished tooth surface. The ends of the orthodontic wire were clamped in the pulling jaw of the Instron apparatus and pulled at a crosshead speed of 5 mm/min, thereby placing the adhesive bond in shear stress. The force in kilograms (kg) at which the bond failed was recorded, and this number was converted to a force per unit area (units of $kg/cm^2$ or MPa) using the known surface area of the button. Each reported value of adhesion to enamel or adhesion to dentin represents the average of 5 replicates.

Comprehensive Strength (CS) Test Method

Compressive strength was evaluated by first injecting a test sample into a glass tube having a 4 mm inner diameter and length of 4 cm. The ends of the glass tube were plugged with silicone plugs. The filled tubes were subjected to 0.275 megapascal (MPa) pressure for 5 minutes and irradiated with a XL 1500 curing light (3M Company) for 60 seconds. The tube samples were then placed in 37° C. water container for 24 hours. The tubes were cut at a length of 7 mm and the samples were pushed out of the glass tubes. Compressive strength was determined according to ISO Standard 7489 using an INSTRON universal tester (Instron Corp., Canton, Mass.) operated at a crosshead speed of 1 millimeter per minute (mm/min). Results were reported as the average of 5 replicates.

Diametral Tensile Strength (DTS) Test Method

Diametral tensile strength was measured using the above-described CS procedure, but using samples were cut to a length of 2 mm. Results were reported as the average of 5 replicates.

Flexural Strength (FS) Test Method

Flexural strength was evaluated by first injecting a test sample into a glass square tube having a 1-mm inner diameter. The square tubes were irradiated with a XL 1500 curing light (3M Company) for 30 seconds then rotated 180 degrees and irradiated for another 30 seconds. The samples were taken out of the square tubes and placed in 37° C. water for 1 day. Flexural strength was measured using the above-described CS procedure. Results were reported as the average of 5 replicates.

Visual Opacity (MacBeth Values) Test Method

Disc-shaped (1-mm thick×20-mm diameter) paste samples were cured by exposing them to illumination from a VISILUX 2 curing light (3M Company) for 60 seconds. Hardened samples were measured for direct light transmission by measuring transmission of light through the thickness of the disk using a MacBeth transmission densitometer Model TD-903 equipped with a visible light filter, available from MacBeth (MacBeth, Newburgh, N.Y.). Lower MacBeth Values indicate lower visual opacity and greater translucency of a material. The reported values are the average of 3 measurements.

Radiopacity (MacBeth Values) Test Method

The same disc shaped samples used in visual opacity measurements were used in making radiopacity measurements. A piece of x-ray film was placed on a sheet of lead which was 6.394-mm thick. Next, the sample and an aluminum step wedge were placed on top of the x-ray film. The sample, aluminum step wedge, and film were then irradiated with X-rays at 62 kV at a target film distance of 400 mm. The film was then developed using an Air Techniques Peri-Pro X-Ray film developer (Air Techniques, Hicksville, N.Y.). The developed film was then measured using a MacBeth transmission densitometer Model TD-903. The measurements were then plotted against the aluminum step measurements and calculated compared to the thickness of the each aluminum step.

Polish Retention (Toothbrush Abrasion/Gloss) Test Method

Polish Retention: The polish retention of a hardened sample was measured by the following method. Rectangular-shaped paste samples (20-mm long×9-mm wide×3-mm thick) were cured with a VISILUX 2 unit for 60 seconds. The samples were mounted with double-sided adhesive tape (Scotch Brand Tape, Core series 2-1300, St. Paul, Minn.) to a holder and were polished according to the following series of steps that were performed sequentially as shown in the chart below. A Buehler ECOMET 4 Polisher with an AUTOMET 2 Polishing Head was used with clockwise rotation.

Polishing Sequence of Steps

| Step No. | Procedure (Abrasive-Grit) | Lubricant | RPM | Load (Kg) per sample | Time (Seconds) |
|---|---|---|---|---|---|
| 1 | Polish (SiC-320) | Water | 150 | 0.45 | 40 |
| 2 | Rinse | Water | | | |
| 3 | Polish (SiC-600) | Water | 150 | 0.45 | 60 |
| 4 | Rinse | Water | | | |
| 5 | Polish (Master Polish Solution) | Water | 120 | 0.34 | 100 |
| 6 | Rinse | Water | | | |

A micro-tri-gloss instrument (BYK Gardner, Columbia, Md.) was used to collect photoelectric measurements of specularly reflected light from the sample surface after polishing and after toothbrushing. The procedure described in ASTM D 523-89 (Reapproved 1994) Standard Test Method for Specular Gloss, for measurements made at 60° geometry was followed with the following modification. Initial gloss after polishing ($G_I$) was measured for initial sample. Final gloss after 2000 toothbrushing cycles ($G_F$) was measured for the final sample. A ΔG value was calculated with the following formula: $\Delta G = (G_F) - (G_I)$. In addition to the initial and final readings, gloss measurements were read at 500, 1000, and 1500 toothbrush strokes. Each sample was brushed with an ORAL B 40 medium Straight toothbrush (Oral B Laboratories, Belmont, Calif.) using CREST Regular Flavor (Proctor & Gamble, Cincinnati, Ohio) toothpaste. One operator brushed all of the samples using forces on the order of toothbrushing forces. Each sample was brushed with the same toothbrush. One toothbrushing cycle was a forward and a backstroke.

Abbreviations, Descriptions, and Sources of Materials

| Abbreviation | Description and Source of Material |
|---|---|
| AA:ITA | Copolymer made from a 4:1 mole ratio of acrylic acid:itaconic acid, prepared according to Example 3 of U.S. Pat. No. 5,130,347 (Mitra), MW (average) = 106,000; polydispersity ρ = 4.64. |
| IEM | 2-Isocyanatoethyl methacrylate (Sigma-Aldrich, St. Louis, MO) |
| VBCP | Polymer made by reacting AA:ITA copolymer with sufficient IEM to convert 16 mole percent of the acid groups of the copolymer to pendent methacrylate groups, according to the dry polymer preparation of Example 11 of U.S. Pat. No. 5,130,347. |
| BisEMA6 | Ethoxylated (6 mole ethylene oxide) bisphenol A dimethacrylate; SR541; (Sartomer Company, Exton, PA) |
| BisGMA | 2,2-Bis[4-(2-hydroxy-3-methacryloyloxy-propoxy)phenyl]propane; CAS No. 1565-94-2 |
| HEMA | 2-Hydroxyethyl methacrylate (Sigma-Aldrich) |
| DiHEMA-P | Di(hydroxyethyl methacrylate) phosphate (Prepared according to the Preparation described herein) |
| GDMA | Glycerol dimethacrylate (Rohm Tech, Inc., Malden, MA) |
| Ebecryl 1830 | Acrylate oligomer (UCB Radcure, Inc., Atlanta, GA) |
| DMAPE | 4-Dimethylaminophenethanol (Sigma-Aldrich) |
| EDMAB | Ethyl 4-(N,N-dimethylamino)benzoate (Sigma-Aldrich) |
| DPIPF6 | Diphenyliodonium hexafluorophosphate (Johnson Matthey, Alpha Aesar Division, Ward Hill, NJ) |
| CPQ | Camphorquinone (Sigma-Aldrich) |
| ATU | Allylthiourea (Sigma-Aldrich) |
| KPS | Potassium persulfate; $K_2S_2O_8$ (Sigma-Aldrich) |
| FAS Glass I | "Control Glass" as described in Example 1 of U.S. Pat. No. 5,154,762 (Mitra et al.) and subsequently silane-treated as described for Filler FAS I in U.S. Pat. Publication No. 2003/0166740 (Mitra et al.). Average particle size estimated to be 3.0 micrometers, based on the Average Particle Size by Particle Size Analyzer Test Method described herein. |
| FAS Glass II | Same as FAS Glass I, except with an average particle size estimated to be 1.0 micrometers, based on the Average Particle Size by Particle Size Analyzer Test Method described herein. |
| FAS Glass III | Schott Glass (Product No. G 018-117; average particle size 1.0 micrometers; Schott Electronic Packaging, GmbH, Landshut, Germany). The filler was silane-treated as described for Filler FAS VI in U.S. Pat. Publication No. 2003/0166740 (Mitra et al.). |
| Nalco 2329 | Sodium hydroxide stabilized colloidal silica sol (pH about 8–9, nominal particle diameter about 75 nm, solids content about 40%) (Nalco, Naperville, IL) |
| A174 | γ-Methacryloxypropyltrimethoxysilane (Witco Osi Specialties, Danbury, CT) |
| Zirconia Sol | Aqueous zirconia sol containing 23% solids prepared as described in U.S. Pat. No. 5,037,579 (Matchette). Primary particle size was determined to be 5 nm based on the Crystallite Particle Size and Crystal Form Content Test Method described in U.S. Pat. No. 6,387,981 (Zhang et al.), and aggregated particle size was determined to be 50–60 nm based on the Photon Correlation Spectroscopy Test Method described in U.S. Pat. No. 6,387,981 (Zhang et al.). |
| PEGDMA | Polyethylene glycol (400) dimethacrylate; SR603; (Sartomer Co.) |
| TEGDMA | Triethyleneglycol Dimethacrylate; SR205; (Sartomer Co.) |
| UDMA | Diurethane Dimethacrylate; Rohamere 6661-0 (Rohm Tech, Inc., Malden, MA) |

Starting Materials Preparations

DiHEMA-P (Mixture of HEMA Phosphates and Tetra-HEMA Pyrophosphate)

A 1-liter three-necked round-bottomed flask fitted with a reflux condenser with gas inlet, a mechanical stirrer, and an addition funnel with gas outlet was charged with 76.7 g of $POCl_3$ and 500 ml THF. A solution of 130.5 g HEMA, 101.5 g triethylamine (TMA) and 87 g of THF was placed in the addition funnel. The flask was cooled via an ice-water-salt bath to approximately −5° C. The solution was added dropwise with stirring over a period of 25 minutes during which the temperature was maintained between 0° C. and −5° C. The mixture was stirred for three hours allowing the temperature to rise to room temperature. To the flask was added an additional 200 ml of THF to facilitate stirring. To the addition funnel was added a solution of 51 g of TEA and 6.8 g water in 50 ml of THF. After cooling the flask to 0–5° C. via the ice-water-salt bath, the solution was added dropwise during 16 minutes. The mixture was allowed to come to room temperature and stirred for 18 hours. The mixture was filtered to remove the precipitated salts and the THF removed in vaccuo. The product, 168 g, was a light orange liquid which was characterized by $^1H$, $^{13}C$ and $^{31}P$ NMR to be a mixture of mono-, di-, and tri-HEMA phosphate and tetraHEMA pyrophosphate.

Filler A (Silane-Treated Nano-Sized Silica Particles)

Silane-treated, non-aggregated, nano-sized silica particles in the form of a dry powder were prepared according to the following procedure. Nalco 2329 silica sol (400.82 g) was charged to a one-quart jar. Methoxy-2-propanol (250.28 g) and A174 (6.15 g) were mixed together and added to the silica sol with stirring for about 5 minutes. The jar was sealed and heated to 80° C. for 16 hours. The resulting white dispersion was dried using a gap drying process according to the procedures described in U.S. Pat. No. 5,980,697 (Kolb et al.) and U.S. Pat. No. 5,694,701 (Huelsman, et al.), with a dispersion coating thickness of about 35-mil (0.9-mm) and a residence time of 1.6 minutes (heating platen temperature 143° C. and condensing platen temperature 21° C.) to yield a fine, free-flowing white powder that was designated Filler A. The nominal particle diameter of Filler A was assumed to be the same as in the starting Nalco silica sol, i.e., about 75 nanometers (nm).

Filler B (Silane-Treated Silica Clusters)

Silane-treated, nano-sized silica particles loosely aggregated as silica clusters were prepared in the form of a free-flowing dry powder according to the following procedure. Nalco 2329 silica sol (1.0 kg) was spray dried using a 91-cm Niro Spray Drier (Niro MOBILE MINOR Spray Drier, Columbia, Md.) at a 325° C. inlet temperature and a 120° C. outlet temperature. A 330-g sample of the resulting dry solid was added to a 5.5-liter jar mill and ball-milled for 16 hours to yield a white powder that was determined according to the Average Particle Size by Particle Size Analyzer Test Method described herein to consist of silica clusters having an average size of 5 micrometers. Primary silica particles making up the silica clusters were assumed to be the same size as in the starting Nalco 2329 silica sol, i.e., having a nominal particle size of about 75 nanometers.

A 100-g sample of the white powder was thoroughly mixed with deionized water (300 g) by stirring for 2 minutes with a magnetic stir bar. The resulting homogeneous mixture was adjusted to a pH of 8.5 with ammonium hydroxide. A174 (3.5 g) was added, the contents thoroughly mixed for 120 minutes using a magnetic stir bar, and the resulting mixture adjusted to a final pH of 8.25. The mixture was then spray dried using a Buchi spray drier (Buchi/Brinkman Mini Spray Dryer, Model 190, Brinkmann Instruments, Inc., Westbury, N.Y.) at 200° C. inlet temperature and 85° C. outlet temperature. The resulting fine, free-flowing, silane-treated (S/T) white powder was designated Filler B.

Filler C (Silane-Treated Silica-Zirconia Clusters)

Silane-treated, nano-sized silica and zirconia particles loosely aggregated as substantially amorphous clusters were prepared in the form of a dry powder according to the following procedure. A 5.0-kg portion of Nalco 1042 silica sol was adjusted to a pH of 2.5 using dilute nitric acid. The pH-adjusted sol was added slowly to zirconyl acetate (2.95 kg) and the resulting mixture stirred for 1 hour. This mixture was then spray dried using a 91-cm Niro Spray Drier (Niro MOBILE MINOR Spray Drier, Columbia, Md.) at a 325° C. inlet temperature and a 120° C. outlet temperature. The resulting solid was heat-treated (calcined) at 550° C. for 4 hours. The calcined solid was ball-milled for 160 hours to yield a white powder that was determined according to the Average Particle Size by Particle Size Analyzer Test Method described herein to consist of clusters having an average size of 2 micrometers.

A 20-g sample of the white powder was thoroughly mixed with deionized (DI) water (40 g) by stirring for 2 minutes with a magnetic stir bar. The resulting homogeneous mixture was adjusted to a pH of 8.5 with ammonium hydroxide. A174 (1.7 g) was added, the contents thoroughly mixed for 120 minutes using a magnetic stir bar, and the resulting mixture adjusted to a final pH of 8.25. The mixture was then spray dried using a Buchi spray drier (Buchi/Brinkman Mini Spray Dryer, Model 190, Brinkmann Instruments, Inc., Westbury, N.Y.) at 200° C. inlet temperature and 85° C. outlet temperature. The resulting fine, free-flowing white powder was designated Filler C.

Filler D (Silane-Treated Nano-Sized Zirconia Particles)

Zirconia Sol (800.0 g; 184 g zirconia) and MEEAA (72.08 g) were charged to a 1-liter round-bottom flask. The water and acid were removed via rotary evaporation to afford a powder (291.36 g) that was further dried in a forced-air oven (90° C.) to provide a dried powder (282.49 g). Deionized (DI) water (501.0 g.) was added and the powder redispersed. The resulting dispersion was charged to a 2-liter beaker followed by the addition with stirring of 1-methoxy-2-propanol (783 g; Sigma-Aldrich), SILQUEST A-174 (83.7 g) and SILQUEST A-1230 (56.3 g). The resulting mixture was stirred 30 minutes at room temperature and then separated into two quart jars and sealed. The jars were heated to 90° C. for 4.0 hours, and the contents concentrated via rotary evaporation to afford a liquid concentrate (621 g).

DI water (2400 g) and concentrated ammonia/water (80.0 g; 29% $NH_3$) were charged to a 4-liter beaker followed by the addition over about 5 minutes of the liquid concentrate to afford a white precipitate. The precipitate was recovered by vacuum filtration and washed with DI water. The resulting wet cake was dispersed in 1-methoxy-2-propanol (661 g) to afford a dispersion that contained 15.33 weight % zirconia. The silane-treated nanozirconia filler was designated Filler D.

The primary and aggregated particle sizes of Filler D were assumed to be the same as in the starting Zirconia Sol, i.e., about 5 nanometers and 50–60 nanometers, respectively.

Examples 1–18

Dental Fillers Including Acid-Reactive Oxyfluoride Nanostructured Materials

Example 1

Aluminum-Strontium-Oxyfluoride Materials

A 2 molar DI water solution of aluminum nitrate (80 ml) was added to a 2 molar DI water solution of strontium nitrate (20 ml) to afford a "cation" solution. A 2 molar DI water solution of ammonium hydroxide (720 ml) was added to a 2 molar DI water solution of ammonium fluoride (180 ml) to afford an "anion" solution. The "cation" solution was rapidly added with rapid stirring to the "anion" solution. The resulting precipitated white powder was collected using vacuum Buchner filtration onto coarse filter paper and washed with DI water. The resulting water-wet solids material ("wet-cake") was designated Example 1. All starting compounds were obtained from Sigma-Aldrich.

Examples 2–6

Heat-Treated Aluminum-Strontium-Oxyfluoride Materials

Oxyfluoride materials were made as described in Example 1, except the amounts of the cation and anion solutions were varied. The amounts of starting solution volumes for Examples 2–6 are provided in Table 1A. The precipitates were dried at 100° C. overnight, heated to 250° C. for 1 hour, ground with mortar and pestle, and passed through a 150-mesh sieve to afford white powders designated as Example 2–6. The calculated cation and anion molar ratios, the fluoride content, and surface areas of the filler powders were determined according to the Test Methods described herein and the results are provided in Table 1C. Particle size analysis was performed on the heat-treated precipitate (Example 3) according to the Average Particle Size by Particle Size Analyzer Test Method described herein and calculated to be 7.35 micrometers.

Examples 7–10

Heat-Treated Aluminum-Strontium-Silicon-Oxyfluoride Materials

Oxyfluoride materials were made as described for Example 1 with the following modifications in procedure in order to include silica. Aqueous sodium silicate solution (SS Solution) containing 14 weight % sodium hydroxide and 27 weight % silica (Sigma-Aldrich) was diluted with DI water to form a sodium silicate solution containing 2 moles of sodium hydroxide and 2 moles of silica per liter. For example, 100 g of the commercially available SS Solution containing 27 g of silica and 14 g of sodium hydroxide has 0.45 moles of silica and 0.45 moles of sodium hydroxide. To prepare the 2 molar sodium silicate solution, the SS Solution was diluted with DI water to a final solution volume of 225 ml.

Precipitation reactions were carried out as described for Examples 2–6, except that the 2 molar sodium silicate solution was substituted for part of the ammonium hydroxide solution, as indicated in Table 1B under the heading "base solutions". Table 1B indicates the amounts of each the solutions used for Examples 7–10. The precipitates were dried, heated, and ground as described above for Examples 2–6. The calculated cation and anion molar ratios and the fluoride content of the filler powders (Examples 7–10) were determined according to the Test Methods described herein and the results provided in Table 1C.

For comparison, Table 1C also provides the fluoride content values for conventional FAS (fluoroaluminosilicate) glass materials (Comparative Examples CE-1, CE-2, and CE-3) prepared from melt processes. Table 1C also provides calculated fluoride contents for two hypothetical compositions as reference values. As indicated, the fluoride content of an "80/20 mole % Al/Sr" Al—Sr—O—F material with all oxygen present as hydroxyl groups, and with F comprising half of the anions would have an F content of 29.6%. A pure fluoride compound of the same cation composition would be 60.4 wt. % F. The filler samples in Table 1C have fluoride contents ranging from 11.5 to 50 weight %.

TABLE 1A

| | Cation Water Solutions (2 molar) Starting Volumes (ml) | | Anion Water Solutions (2 molar) Starting Volumes (ml) | |
|---|---|---|---|---|
| Example | Aluminum Nitrate | Strontium Nitrate | Ammonium Hydroxide | Ammonium Fluoride |
| 2 | 80 | 20 | 810 | 90 |
| 3 | 80 | 20 | 720 | 180 |
| 4 | 80 | 20 | 585 | 315 |
| 5 | 80 | 20 | 450 | 450 |
| 6 | 80 | 20 | 180 | 720 |

TABLE 1B

| | Cation Water Solutions (2 molar) Starting Volumes (ml) | | Base Water Solutions (2 molar) Starting Volumes (ml) | | |
|---|---|---|---|---|---|
| Example | Aluminum Nitrate | Strontium Nitrate | Sodium Silicate | Ammonium Hydroxide | Ammonium Fluoride |
| 7 | 67 | 33 | 67 | 653 | 180 |
| 8 | 67 | 33 | 67 | 383 | 450 |
| 9 | 63 | 37 | 25 | 695 | 180 |
| 10 | 63 | 37 | 25 | 425 | 450 |

TABLE 1C

| Example | Cation Molar Ratio (Al/Sr/Si) | Anion Molar Ratio (OH/F) | Fluoride Content (Weight %) | Surface Area (m$^2$/g) |
|---|---|---|---|---|
| 2 | 80/20/0 | 90/10 | 11.50 | 128 |
| 3 | 80/20/0 | 80/20 | 20.70 | 109 |
| 4 | 80/20/0 | 65/35 | 31.90 | 111 |
| 5 | 80/20/0 | 50/50 | 40.70 | 34 |
| 6 | 80/20/0 | 20/80 | 50.00 | 15 |
| 7 | 40/20/40 | 80/20 | 16.30 | NT[a] |
| 8 | 40/20/40 | 50/50 | 31.20 | NT |
| 9 | 50/30/20 | 80/20 | 12.80 | NT |
| 10 | 50/30/20 | 50/50 | 27.30 | NT |
| CE-1 | FAS Glass I | | 19.9 | 2 |
| CE-2 | FAS Glass II | | 17.8 | NT |
| CE-3 | FAS Glass III | | 16.8 | 5 |
| 80 mole % Al(OH)$_{0.75}$(F)$_{0.75}$/20% Sr(OH)(F) (calculated theoretical) | | | 29.6 | — |
| 80 mole % AlF$_3$/20% SrF$_2$ (calculated theoretical) | | | 60.4 | — |

[a]NT—Not Tested

Example 11

Porous Aggregates of Particles Containing Acid-Reactive Oxyfluoride Material ("Clusters" of Silica Nanoparticles)

Acid-reactive oxyfluoride filler material was coated onto or infiltrated into clusters of nanosized silica particles according to the following procedure. "Cation" and "anion" solutions were prepared as described for Example 1. Filler B (7 g; S/T silica clusters) was added to the "anion" solution and the resulting solution stirred for 10 minutes. The "cation" solution was then added with rapid stirring to the "anion" solution. The resulting precipitated white powder was collected, dried, heated, ground and sieved as described for Examples 2–6 to afford a white powder designated as Example 11 filler. The "clusters" to acid-reactive oxyfluoride material weight ratio of the Example 11 filler was about 1 to 2.

Example 12

Porous Aggregates of Particles Containing Acid-Reactive Oxyfluoride Material ("Clusters" of Silica-Zirconia Nanoparticles)

Acid-reactive oxyfluoride filler material was coated onto or infiltrated into clusters of nanosized silica-zirconia particles according to the following procedure. "Cation" and "anion" solutions were prepared as described for Example 1. Filler C (7 g; S/T silica-zirconia clusters) was added to the "anion" solution and the resulting solution stirred for 10 minutes. The "cation" solution was then added with rapid stirring to the "anion" solution. The resulting precipitated white powder was collected, dried, heated, ground and sieved as described for Examples 2–6 to afford a white powder designated as Example 12 filler. The "clusters" to acid-reactive oxyfluoride material weight ratio of the Example 12 filler was about 1 to 2.

Example 13

Ball-Milled Oxyfluoride Material

An acid-reactive oxyfluoride material was prepared as described in Example 1. After precipitation, filtering, and washing, the water-wet precipitate was heated at 250° C. for 1 hour. The heat-treated precipitate was then added to DI water to form a 25% by weight suspension. This suspension was ball milled for 72 hours using ¼ inch alumina media. The resulting milled suspension was collected and centrifuged at 10,000 rpm for 10 minutes. The wet cake was removed from the centrifuge tubes and further dewatered by hand pressing between sheets of coarse (hardened) filter paper to a concentrate of 50% by weight water to afford a stiff, clay-like mass that was designated Example 13. Portions of the clay-like material were readily dispersible in the resin components of Paste A compositions (See Table 4A). Particle size analysis was performed according to the Average Particle Size by Particle Size Analyzer Test Method described herein on the ball milled suspension and calculated to be 1.31 micrometers.

Example 14A

Attritor-Milled Oxyfluoride Material

An acid-reactive oxyfluoride material was prepared as described in Example 1 and subsequently milled by using a laboratory Attritor Mill (Union Process, Model 01, Akron, Ohio). After precipitation, filtering, and washing, the water-wet precipitate was heated at 250° C. for 1 hour. In preparation for milling, the heat-treated precipitate was added to DI water to form a 10% by weight suspension. This suspension was attritor-milled for 1 hour using 2-mm $ZrO_2$ media at 100% power. The resulting milled suspension was collected and centrifuged at 10,000 rpm for 10 minutes. The wet cake was removed from the centrifuge tubes and further dewatered by hand pressing between sheets of coarse (hardened) filter paper to a concentrate of 50% by weight water to afford a stiff, clay-like mass that was designated Example 14A. Portions of the clay-like material were readily dispersible in the resin components of Paste A compositions (See Table 4B). Particle size analysis was performed according to the Average Particle Size by Particle Size Analyzer Test Method described herein on the attritor-milled suspension and calculated to be 0.871 micrometers.

Example 14B

Optimized Attritor-Milled Oxyfluoride Material

An acid-reactive oxyfluoride material was prepared as described in Example 1 and subsequently milled by using a laboratory Attritor Mill (Union Process, Model 01). After precipitation, filtering, and washing, the water-wet precipitate was heated at 250° C. for 1 hour. In preparation for milling, the heat-treated precipitate was added to DI water to form a 10% by weight suspension. This suspension was attritor-milled for 2 hours using 0.5-mm and 2-mm $ZrO_2$ media at a 25/75 ratio and run at 100% power. The resulting milled suspension was collected and centrifuged at 9,600 rpm for 6 minutes. The wet cake was removed from the centrifuge tubes and further dewatered by hand pressing between sheets of coarse (hardened) filter paper to a concentrate of 50% by weight water to afford a stiff, clay-like mass that was designated Example 14B. Portions of the clay-like material were readily dispersible in the resin components of Paste A compositions (See Table 4C). Particle size analysis was performed according to the Average Particle Size by Particle Size Analyzer Test Method described herein on the optimized attritor milled suspension and calculated to be 0.163 micrometers.

Example 15

Non-Dried Oxyfluoride Material

An acid-reactive oxyfluoride material was prepared as described in Example 1. The non-dried precipitate was then centrifuged at 9,600 rpm for 6 minutes. The wet cake was removed from the centrifuge tubes and further dewatered by hand pressing between sheets of coarse (hardened) filter paper to a concentrate of 50% by weight water to afford a stiff, clay-like mass that was designated Example 15. Portions of the clay-like material were readily dispersible in the resin components of Paste A compositions (See Table 4C).

Examples 16–18

Oxyfluoride Material Containing Other Metal Ions

Acid-reactive oxyfluoride materials were prepared as described in Example 1, but substitutions were made in composition to include such ions as La, Y, and Ca. Further processing was achieved according to the milling/centrifuging/dewatering processes described in Example 14B to afford stiff, clay-like masses that were designated Examples 16–18. Solution amounts are shown below in Table 2. Portions of the clay-like material (Example 16–18) were readily dispersible in the resin components of Paste A compositions (See Table 4C). Particle size analysis was performed according to the Average Particle Size by Particle Size Analyzer Test Method described herein on the optimized attritor milled suspension of Example 16 and calculated to be 0.2 micrometers.

TABLE 2

| | Cation Water Solutions (2 molar) Starting Volumes (ml) | | Anion Water Solutions (2 molar) Starting Volumes (ml) | |
| --- | --- | --- | --- | --- |
| | Trivalent | | | |
| Example | Metal Nitrate | Divalent Metal Nitrate | Ammonium Hydroxide | Ammonium Fluoride |
| 16 | 80 (La) | 20 (Sr) | 720 | 180 |
| 17 | 80 (Y) | 20 (Sr) | 720 | 180 |
| 18 | 80 (Al) | 20 (Ca) | 720 | 180 |

Evaluations and Results—Oxyfluoride Materials

Evaluation of Oxyfluoride Material Curing Efficiency

Oxyfluoride filler materials (Examples 3, 7, and 11) were prepared without grinding and sieving steps and were combined with a Test Resin and evaluated for curing efficiency according to the Test Method described herein. Results are provided in Table 3A and compared with curing results for conventional glass fillers (Comparative Examples CE-1 to CE-3). The set of 4 numbers represent the curing efficiency in terms of qualitative extent of cure (based on a 0–5 scale, see Test Method) after 1 hour, 1 day, 2 days, and 3 days.

TABLE 3A

| Filler Example | Qualitative Extent of Cure at Indicated Ratio of Filler to Resin (by Wt.) (After 1 Hour, 1 Day, 2 Days, 3 Days) | | | |
|---|---|---|---|---|
| | 1 to 4 Ratio | 1 to 2 Ratio | 1 to 1 Ratio | 2 to 1 Ratio |
| 3 | 0, 1, 3, 4 | 1, 5, 5, 5 | NT[a] | NT |
| 7 | NT | 2, 4, 5, 5 | NT | NT |
| 11 | NT | 1, 4, 5, 5 | NT | NT |
| CE-1 | 0, 2, 3, 3+ | 1, 3, 4, 5 | NT | 4, 5, 5, 5 |
| CE-2 | NT | 2, 4, 4, 5 | 3, 5, 5, 5 | NT |
| CE-3 | 0, 2, 3, 3 | 2, 4, 4, 5 | NT | NT |

[a]NT—Not Tested

In a similar manner, additional oxyfluoride filler materials of Example 3 were prepared with grinding and sieving (150 mesh) and were evaluated for curing efficiency as described in the preceding paragraph. Results for Example 3 prepared with grinding and sieving and for Examples 16–18 (optimized attritor-milled samples) are provided in Table 3B. For these samples, the set of 4 numbers represent the curing efficiency in terms of qualitative extent of cure (based on a 0–5 scale, see Test Method) after 1 hour, 3 hours, 5 hours, and 7 hours.

TABLE 3B

| Filler Example | Qualitative Extent of Cure at Indicated Ratio of Filler to Resin (by Wt.) (After 1 Hour, 3 Hours, 4 Hours, 7 Hours) | |
|---|---|---|
| | 1 to 4 Ratio | 1 to 2 Ratio |
| 3 | 3, 4, 4, 5 | 5, 5, 5, 5 |
| 16 | 2, 4, 4, 4 | NT |
| 17 | 2, 4, 5, 5 | NT |
| 18 | 0, 4, 5, 5 | NT |

[a]NT—Not Tested

Comparing the data in Tables 3A and 3B, it is noted that cure times decreased dramatically for Example 3 prepared with grinding and sieving as compared to Example 3 without grinding and sieving. The former showed significant curing in 1–4 hours at only 20% loading (1:4 ratio), whereas the latter took 3 days to fully cure. Examples 16–18 (milled samples) were also fully cured at 3 hours. Full curing of Example 3 prepared with grinding and sieving was observed in 1 hour at the 33% loading (1:2 ratio) as compared to 1 day for Example 3 without grinding and sieving.

Hence, comparison of the data in Tables 3A and 3B shows that the precipitated acid-reactive oxyfluoride filler materials (following grinding or milling) have high curing efficiency in comparison with conventional melt processed glass fillers or oxyfluoride materials that have not been ground or milled. Therefore, it is concluded that at least some degree of dispersion is required to observe the high curing efficiency imparted by the high surface area fillers. Coarse, heat-treated granules of oxyfluoride materials exhibited curing efficiency similar to the conventional glasses. Simple grinding and sieving (150 mesh) of the coarse granules (i.e., agglomerates) significantly increased the curing efficiencies of the acid-reactive oxyfluoride filler materials. Milled acid-reactive oxyfluoride filler materials with La or Y cations (instead of Al) or with Ca cations (instead of Sr) also exhibited high curing efficiencies.

Example 19

Two-Part Compositions

First Paste Compositions (Pastes A1–A20)

Acid-reactive oxyfluoride filler material was prepared as described in Example 13. The resulting clay-like material comprising 50 weight % water was formulated into first paste compositions A1–A5 as described below.

Acid-reactive oxyfluoride filler material was also prepared as described in Example 14A. The resulting clay-like material comprising 50 weight % water was formulated into first paste compositions A6–A13 as described below.

Acid-reactive oxyfluoride filler material was also prepared as described in Example 14B. The resulting clay-like material comprising 50 weight % water was formulated into first paste compositions A14–A15, A17–A18, and A20 as described below. Similarly, the filler material of Example 15 was prepared and formulated into first paste composition A16; and the filler material of Example 16 was prepared and formulated into first paste composition A19.

First paste compositions (Pastes A1–A20) were prepared by combining the ingredients (indicated as parts by weight) that are listed in Tables 4A, 4B, and 4C. The compositions were prepared by weighing out the correct amounts of HEMA, DMAPE, and ATU, and then speed mixing for 30 seconds. Next, the next ingredients CPQ and EDMAB were added followed by speed mixing for 30 seconds. Next, the PEGDMA was added followed by speed mixing for 30 seconds. At this time, the acid-reactive nano-sized filler (Example 1) and DI water (processed together in a "clay" form, as described in Examples 13–16) were added. The resulting mixture was hand mixed and speed mixed until homogeneous. The last step was to add any optional non-reactive filler components (e.g., Filler A–Filler D) and speed mix an additional minute or until the paste was homogeneous. The compositions of Pastes A1–A5 are provided in Table 4A, the compositions of Pastes A6–A13 are provided in Table 4B, and the compositions of Pastes A14–A20 are provided in Table 4C.

TABLE 4A

| Paste A Compositions (Parts by Weight) | | | | | |
|---|---|---|---|---|---|
| Ingredient | A1 | A2 | A3 | A4 | A5 |
| DI Water | 2.918 | 2.918 | 2.918 | 3.063 | 3.063 |
| HEMA | 1.594 | 1.594 | 1.594 | 1.686 | 1.686 |
| PEGDMA | 1.845 | 1.845 | 1.845 | 1.952 | 1.952 |
| DMAPE | 0.084 | 0.084 | 0.084 | 0.089 | 0.101 |
| ATU | 0.084 | 0.084 | 0.084 | 0.089 | 0.101 |
| CPQ | 0.279 | 0.279 | 0.279 | 0.03 | 0.034 |
| EDMAB | 0.279 | 0.279 | 0.279 | 0.03 | 0.034 |
| Example 13 (Acid-Reactive Filler) | 2.918 | 2.918 | 2.918 | 3.063 | 3.063 |
| Filler A (Non-Acid Reactive Si Filler) | 1.0 | 0 | 1.5 | 0 | 0 |

TABLE 4B

Paste A Compositions (Parts by Weight)

| Ingredient | A6 | A7 | A8 | A9 | A10 | A11 | A12 | A13 |
|---|---|---|---|---|---|---|---|---|
| DI Water | 1.189 | 1.189 | 1.189 | 0.800 | 1.000 | 0.983 | 1.189 | 1.189 |
| HEMA | 0.655 | 0.655 | 0.655 | 0.655 | 0.745 | 0.574 | 0.655 | 1.185 |
| PEGDMA | 0.758 | 0.758 | 0.758 | 0.758 | 0.758 | 0.656 | 0.758 | 0.758 |
| DMAPE | 0.039 | 0.039 | 0.039 | 0.039 | 0.039 | 0.084 | 0.039 | 0 |
| ATU | 0.039 | 0.039 | 0.039 | 0.039 | 0.039 | 0.084 | 0.039 | 0 |
| CPQ | 0.013 | 0.013 | 0.013 | 0.013 | 0.013 | 0.005 | 0.013 | 0.01 |
| EDMAB | 0 | 0 | 0 | 0 | 0 | 0 | 0 | 0.01 |
| Example 14A (Acid-Reactive Filler) | 1.189 | 1.189 | 1.189 | 0.800 | 1.000 | 0.983 | 1.189 | 1.189 |
| Filler A (Non-Reactive Si Filler) | 0 | 0 | 0 | 0 | 3.400 | 1.250 | 3.500 | 1.35 |
| Filler B (Non-Reactive Si "Clusters") | 0 | 0 | 0 | 0 | 0 | 0 | 0 | 3.35 |
| Filler D (Non-Reactive Zr Filler) | 4.220 | 1.584 | 0 | 1.584 | 1.584 | 4.220 | 1.584 | 4.224 |

TABLE 4C

Paste A Compositions (parts by weight)

| Ingredient | A14 | A15 | A16 | A17 | A18 | A19 | A20 |
|---|---|---|---|---|---|---|---|
| DI H2O | 1.189 | 1.189 | 1.07 | 1.189 | 1.189 | 1.189 | 1.189 |
| HEMA | 0.655 | 0.655 | 0.655 | 0.655 | 1.158 | 1.158 | 1.385 |
| PEDGMA | 0.758 | 0.758 | 0.758 | 0.758 | 0.758 | 0.758 | 1.086 |
| DMAPE | 0 | 0 | 0 | 0.039 | 0 | 0 | 0.039 |
| ATU | 0 | 0 | 0 | 0.039 | 0 | 0 | 0.039 |
| CPQ | 0.01 | 0.01 | 0.01 | 0.01 | 0.01 | 0.01 | 0.01 |
| EDMAB | 0.01 | 0.01 | 0.01 | 0 | 0.01 | 0.01 | 0 |
| Example 14B (Acid-Reactive Filler) | 1.189 | 1.189 | 0 | 1.189 | 1.189 | 0 | 1.189 |
| Example 15 (Acid-Reactive Filler) | 0 | 0 | 0 | 0 | 0 | 1.189 | 0 |
| Example 16 (Acid-Reactive Filler) | 0 | 0 | 1.308 | 0 | 0 | 0 | 0 |
| Filler A (Non-Reactive Si Filler) | 1.00 | 1.00 | 1.00 | 1.00 | 1.35 | 1.35 | 0 |
| Filler B (Non-Reactive Si "Clusters") | 0 | 0 | 0 | 0 | 3.35 | 3.35 | 3.00 |
| Filler C (Non-Reactive Zr—Si "Clusters") | 0 | 0 | 0 | 0 | 0 | 0 | 2.5 |
| Filler D (Non-Reactive Zr Filler) | 1.584 | 4.224 | 4.224 | 4.224 | 2.274 | 4.224 | 1.584 |

Second Paste Compositions (Pastes B1–B21)

Second paste compositions (Pastes B1–B21) were prepared by combining the ingredients (indicated as parts by weight) that are listed in Tables 5A, 5B, and 5C. The compositions were prepared by dissolving the VBCP in HEMA, then adding DPIPF6 and speed mixing for 30 seconds. For paste compositions B1–B4, Di-HEMA-P, GDMA/Bis-GMA (premixed together), and Ebecryl 1830 were added followed by speed mixing for 60 seconds. In paste compositions B5–B21, Di-HEMA-P, BisGMA UDMA/TEGDMA/BisEMA6 (premixed together), and Ebecryl 1830 were added followed by speed mixing for 60 seconds. Next, KPS was added followed by speed mixing for 60 seconds. The paste was then speed mixed for 30 seconds. The last step was to add any optional non-reactive filler components (e.g., Filler A–Filler C) and speed mix an additional minute or until the paste was homogeneous. The compositions of Pastes B1–B5 are provided in Table 5A, the compositions of Pastes B6–B14 are provided in Table 5B, and the compositions of Pastes B15–B21 are provided in Table 5C.

TABLE 5A

Paste B Compositions (Parts by Weight)

| Ingredient | B1 | B2 | B3 | B4 | B5 |
|---|---|---|---|---|---|
| HEMA | 1.40 | 1.40 | 1.785 | 1.40 | 1.52 |
| DiHEMA-P | 1.38 | 1.38 | 0.7 | 1.38 | 0.7 |
| VBCP | 0.60 | 0.60 | 0.89 | 0.60 | 1.01 |
| GDMA | 0.81 | 0.81 | 0.81 | 0.81 | 0 |
| Bis-GMA | 0.49 | 0.49 | 0.49 | 0.49 | 0.325 |
| UDMA | 0 | 0 | 0 | 0 | 0.455 |
| BisEMA6 | 0 | 0 | 0 | 0 | 0.455 |
| TEGDMA | 0 | 0 | 0 | 0 | 0.065 |
| DPIPF6 | 0.025 | 0.025 | 0.025 | 0.025 | 0.025 |
| KPS | 0.20 | 0.20 | 0.20 | 0.20 | 0 |
| Ebecryl 1830 | 0.10 | 0.10 | 0.10 | 0.10 | 0.10 |
| Filler A (Non-Reactive Si Filler) | 5.0 | 10.0 | 5.0 | 10 | 5.53 |
| Filler B (Non-Reactive Si "Clusters") | 0 | 0 | 0 | 0 | 2.30 |

TABLE 5B

Paste B Compositions (Parts by Weight)

| Ingredient | B6 | B7 | B8 | B9 | B10 | B11 | B12 | B13 | B14 |
|---|---|---|---|---|---|---|---|---|---|
| HEMA | 1.760 | 1.760 | 1.760 | 1.760 | 1.850 | 1.950 | 1.620 | 2.036 | 1.85 |
| DiHEMA-P | 1.400 | 1.400 | 1.400 | 1.400 | 0.700 | 0.700 | 0.700 | 0.700 | .700 |
| VBCP | 0.950 | 0.950 | 0.950 | 0.950 | 1.000 | 1.050 | 1.050 | 1.010 | 1.000 |
| bisGMA | 0.325 | 0.325 | 0.325 | 0.325 | 0.325 | 0.325 | 0.325 | 0.217 | 0.217 |
| UDMA | 0.455 | 0.455 | 0.455 | 0.455 | 0.455 | 0.455 | 0.455 | 0.303 | 0.303 |
| BisEMA6 | 0.455 | 0.455 | 0.455 | 0.455 | 0.455 | 0.455 | 0.455 | 0.303 | 0.303 |
| TEGDMA | 0.065 | 0.065 | 0.065 | 0.065 | 0.065 | 0.065 | 0.065 | 0.043 | 0.043 |
| DPIPF6 | 0.025 | 0.025 | 0.025 | 0.025 | 0.025 | 0.025 | 0.025 | 0.025 | 0.025 |
| KPS | 0.200 | 0.200 | 0.200 | 0.200 | 0.200 | 0.200 | 0.200 | 0.200 | 0.200 |

TABLE 5B-continued

Paste B Compositions (Parts by Weight)

| Ingredient | B6 | B7 | B8 | B9 | B10 | B11 | B12 | B13 | B14 |
|---|---|---|---|---|---|---|---|---|---|
| Ebecryl 1830 | 0.100 | 0.100 | 0.100 | 0.100 | 0.100 | 0.100 | 0.100 | 0.100 | 0.100 |
| Filler A (Non-Reactive Si Filler) | 5.000 | 0 | 7.500 | 2.500 | 0 | 0 | 0 | 7.500 | 10.000 |
| Filler C (Non-Reactive Zr—Si "Clusters") | 0 | 5.000 | 0 | 7.500 | 7.500 | 7.500 | 4.500 | 0 | 0 |

TABLE 5C

Paste B Compositions (Parts by Weight)

| Ingredient | B15 | B16 | B17 | B18 | B19 | B20 | B21 |
|---|---|---|---|---|---|---|---|
| HEMA | 1.8525 | 1.8525 | 1.8525 | 1.8525 | 1.5156 | 1.5156 | 1.8525 |
| DiHEMA-P | 0.700 | 0.700 | 0.700 | 0.700 | 0.700 | 0.700 | 0.700 |
| VBCP | 0.9975 | 0.9975 | 0.9975 | 0.9975 | 1.0104 | 1.0104 | 0.9975 |
| DPIPF6 | 0.025 | 0.025 | 0.025 | 0.025 | 0.025 | 0.025 | 0.025 |
| Bis-GMA | 0.325 | 0.325 | 0.325 | 0.325 | 0.325 | 0.325 | 0.325 |
| UDMA | 0.455 | 0.455 | 0.455 | 0.455 | 0.455 | 0.455 | 0.455 |
| BisEMA6 | 0.455 | 0.455 | 0.455 | 0.455 | 0.455 | 0.455 | 0.455 |
| TEGDMA | 0.065 | 0.065 | 0.065 | 0.065 | 0.065 | 0.065 | 0.065 |
| KPS | 0 | 0 | 0 | 0.200 | 0 | 0 | 0.150 |
| Ebecrly 1830 | 0.100 | 0.100 | 0.100 | 0.100 | 0.100 | 0.100 | 0.100 |
| Filler A (Non-Reactive Si Filler) | 7.500 | 10.500 | 7.500 | 7.500 | 6.720 | 5.530 | 5.000 |
| Filler B (Non-Reactive Si "Clusters") | 0 | 0 | 0 | 0 | 0 | 2.300 | 0 |
| Filler C (Non-Reactive Zr—Si "Clusters") | 0 | 0 | 0 | 0 | 0 | 0 | 2.300 |

Evaluations and Results—Paste—Paste Composition

Evaluation of Hardened Paste—Paste Compositions

Combined paste—paste compositions were prepared by spatulating a weighed quantity of a freshly prepared first paste composition (Paste A) with a weighed quantity of a freshly prepared second paste composition (Paste B) for 25 seconds. The resulting compositions were designated as test samples and evaluated for one or more of the following tests: Compressive Strength (CS), Diametral Strength (DTS), Flexural Strength (FS), Adhesion to Dentin (DA), Adhesion to Enamel (EA), Visual Opacity (VO), Radiopacity (RO), Polish Retention, and Fluoride Release according to the Test Methods described herein. The quantities of pastes utilized and the subsequent testing results are reported in Tables 6A (Runs 1–8), 6B (Runs 9–19), and 6C (Runs 20–26); and in text following the Tables.

TABLE 6A

Paste—Paste Compositions and Testing Results

| Run | First Paste A (pbw) | Second Paste B (pbw) | CS (MPa) | DTS (MPa) | DA (MPa) | EA (MPa) | VO |
|---|---|---|---|---|---|---|---|
| 1 | A1 (0.76) | B1 (1.0) | 278 | NT[a] | 2.52 | NT | 0.26 |
| 2 | A2 (0.46) | B2 (1.5) | 312 | NT | 4.43 | NT | 0.22 |
| 3 | A1 (0.76) | B2 (1.5) | 384 | NT | 5.87 | NT | 0.26 |
| 4 | A3 (0.91) | B1 (1.0) | 294 | NT | NT | NT | 0.39 |
| 5 | A4 (0.465) | B3 (1.0) | 272 | 29.5 | 6.35 | 6.6 | 0.28 |
| 6 | A4 (0.465) | B4 (1.0) | 316 | 33.1 | 4.56 | NT | 0.35 |
| 7 | A5 (0.465) | B1 (1.25) | 311 | 43.7 | 5.68 | 6.69 | 0.34 |
| 8 | A5 (0.465) | B2 (1.75) | 370 | 45.1 | 4.56 | 6.26 | 0.29 |

[a]NT—Not Tested

TABLE 6B

Paste—Paste Compositions and Testing Results

| Run | Paste A (pbw) | Paste B (pbw) | CS (MPa) | DTS (MPa) | FS (MPa) | DA (MPa) | EA (MPa) | VO | RO |
|---|---|---|---|---|---|---|---|---|---|
| 9 | A6 (0.973) | B6 (1.073) | NT[a] | NT | NT | 2.17 | 3.48 | 0.38 | 1.72 |
| 10 | A7 (0.656) | B6 (1.073) | 324 | 38.1 | NT | 5.58 | 7.08 | 0.35 | 0.93 |
| 11 | A8 (0.466) | B7 (1.073) | NT | 52.1 | NT | 5.01 | 10.78 | 0.38 | 0.97 |
| 12 | A7 (0.656) | B8 (1.323) | 348 | 45.3 | NT | 2.70 | 6.31 | 0.32 | 0.98 |
| 13 | A8 (0.466) | B9 (1.573) | NT | NT | NT | 3.78 | 6.30 | 0.35 | 1.02 |
| 14 | A7 (0.656) | B10 (1.268) | 275 | 41.5 | NT | 4.91 | 7.91 | 0.42 | 1.56 |
| 15 | A9 (0.563) | B11 (1.283) | NT | NT | NT | 2.56 | 3.17 | 0.36 | 1.54 |
| 16 | A10 (1.029) | B12 (0.953) | 263 | 52.8 | NT | 1.13 | 6.17 | 0.41 | 1.03 |
| 17 | A11 (1.061) | B13 (1.252) | 322 | 44.2 | NT | NT | NT | 0.44 | 1.49 |
| 18 | A12 (1.060) | B14 (1.000) | 334 | 41.4 | 47.6 | NT | NT | 0.32 | NT |
| 19 | A13 (1.592) | B5 (1.248) | 312 | 108 | NT | NT | NT | 0.34 | 1.66 |

[a]NT—Not Tested

TABLE 6C

Paste—Paste Compositions and Testing Results

| Run | Paste A (pbw) | Paste B (pbw) | CS (MPa) | DTS (MPa) | FS (MPa) | DA (MPa) | EA (MPa) | VO | RO |
|---|---|---|---|---|---|---|---|---|---|
| 20 | A13 (0.767) | B15 (1.248) | 305 | 88 | 45 | 3.13 | 4.82 | 0.30 | 0.78 |
| 21 | A15 (1.084) | B16 (1.448) | 328 | 74 | 69 | NT[a] | NT | 0.38 | 1.49 |
| 22 | A16 (1.084) | B17 (1.248) | 236 | 49 | NT | NT | NT | 0.41 | 1.73 |
| 23 | A17 (0.192) | B18 (1.468) | 303 | 55 | NT | NT | NT | 0.48 | 1.3 |
| 24 | A18 (1.358) | B19 (1.137) | 313 | 111 | 102 | 0 | 4.59 | 0.31 | 1.31 |
| 25 | A19 (1.592) | B20 (1.248) | 303 | 70 | NT | NT | NT | NT | NT |
| 26 | A20 (1.443) | B21 (1.243) | 292 | 80 | 66 | 4.14 | 5.63 | 0.39 | 1.61 |

[a]NT—Not Tested

The data provided in Tables 6A–6C show that hardened paste-paste compositions containing an acid-reactive oxyfluoride filler material of the present invention demonstrate high mechanical strength (as evidenced by the high CS, DTS and FS values) and good to excellent visual aesthetics (as evidenced by the low visual opacity values).

The data provided in Tables 6B–6C show that the use of nanosized zirconia fillers in combination with the acid-reactive oxyfluoride filler materials can provide hardened compositions with good radiopacity without the loss of visual aesthetics.

Fluoride Release was measured for two of the hardened compositions and found for Run 17 to be 1,100 µg F/g after 29 days, and 1,992 µg F/g after 180 days; and for Run 19 to be 745 µg F/g after 29 days.

Polish Retention was measured for one of the hardened compositions (Run 23) and found to be greater than 80% after 2000 toothbrush strokes.

The complete disclosure of all patents, patent applications, and publications, and electronically available material cited herein are incorporated by reference. The foregoing detailed description and examples have been given for clarity of understanding only. No unnecessary limitations are to be understood there from. The invention is not limited to the exact details shown and described, for variations obvious to one skilled in the art will be included within the invention defined by the claims.

What is claimed is:

1. A composition comprising an oxyfluoride material; wherein the oxyfluoride material is acid-reactive, non-fused, and comprises a trivalent metal, oxygen, fluorine, and an alkaline earth metal; and wherein the composition is a dental filler.

2. The composition of claim 1 wherein the trivalent metal is selected from the group consisting of aluminum, lanthanum, and combinations thereof.

3. A composition comprising an oxyfluoride material; wherein the oxyfluoride material is acid-reactive, non-fused, and comprises aluminum, oxygen, fluorine, and an alkaline earth metal; and wherein the composition is a dental filler.

4. The composition of claim 3 wherein at least 90% by weight of the oxyfluoride material is nanostructured.

5. The composition of claim 4 wherein at least 90% by weight of the oxyfluoride material is in the form of nanoparticles.

6. The composition of claim 5 wherein the nanoparticles are non-aggregated.

7. The composition of claim 5 wherein the nanoparticles are aggregated.

8. The composition of claim 5 wherein the nanoparticles have an average size of at most 100 nanometers.

9. The composition of claim 4 wherein the oxyfluoride material is in the form of a coating on a particle.

10. The composition of claim 9 wherein the particle is a nanoparticle.

11. The composition of claim 9 wherein the particle comprises a metal oxide.

12. The composition of claim 11 wherein the metal oxide is silica.

13. The composition of claim 4 wherein the oxyfluoride material is in the form of a coating on an aggregate of particles.

14. The composition of claim 13 wherein the particles comprise nanoparticles.

15. The composition of claim 13 wherein the particles comprise a metal oxide.

16. The composition of claim 15 wherein the metal oxide is silica.

17. The composition of claim 4 wherein the oxyfluoride material is infiltrated in a porous structure.

18. The composition of claim 17 wherein the porous structure comprises a porous particle.

19. The composition of claim 18 wherein the porous particle comprises a metal oxide.

20. The composition of claim 19 wherein the metal oxide is silica.

21. The composition of claim 17 wherein the porous structure comprises a porous aggregate of particles.

22. The composition of claim 21 wherein the particles are nanoparticles.

23. The composition of claim 21 wherein the particles comprise a metal oxide.

24. The composition of claim 23 wherein the metal oxide is silica.

25. The composition of claim 17 wherein the porous structure comprises a porous coating.

26. The composition of claim 3 wherein the oxyfluoride material further comprises silicon.

27. The composition of claim 3 wherein the oxyfluoride material further comprises a heavy metal.

28. The composition of claim 27 wherein the heavy metal is zirconium.

29. The composition of claim 3 wherein the molar ratio of aluminum to the alkaline earth metal in the oxyfluoride material is at least 50:50 and at most 95:5.

30. The composition of claim 3 wherein the molar ratio of oxygen to fluorine in the oxyfluoride material is at least 50:50 and at most 95:5.

31. The composition of claim 3 wherein the alkaline earth metal is selected from the group consisting of strontium, calcium, barium, and combinations thereof.

32. A composition comprising an oxyfluoride material; wherein the oxyfluoride material is acid-reactive and comprises a trivalent metal, oxygen, fluorine, and an alkaline earth metal, with the proviso that the oxyfluoride material comprises at most 25 mole % silicon based on the total moles of silicon, the trivalent metal, the alkaline earth metal, and any additional cations; and wherein the material is a dental filler.

33. The composition of claim 32 wherein the trivalent metal is selected from the group consisting of aluminum, lanthanum, and combinations thereof.

34. The composition of claim 32 wherein the trivalent metal is aluminum.

35. The composition of claim 34, with the proviso that the oyxfluoride material comprises at most 20 mole % silicon, based on the total moles of silicon, aluminum, and the alkaline earth metal.

36. A dental filler prepared by a method comprising:
combining a first liquid composition comprising a source of a trivalent metal and a source of an alkaline earth metal with a second liquid composition comprising a source of fluorine to provide an acid-reactive oxyfluoride material, wherein the oxyfluoride material comprises the trivalent metal, oxygen, fluorine, and the alkaline earth metal; and
separating the oxyfluoride material from the combined liquid compositions to provide the dental filler.

37. The dental filler of claim 36 wherein the trivalent metal is selected from the group consisting of aluminum, lanthanum, and combinations thereof.

38. The dental filler of claim 36 wherein the trivalent metal is aluminum.

39. A method of preparing a dental filler comprising:
combining a first liquid composition comprising a source of a trivalent metal and a source of an alkaline earth metal with a second liquid composition comprising a source of fluorine to provide an acid-reactive oxyfluoride material, wherein the oxyfluoride material comprises the trivalent metal, oxygen, fluorine, and the alkaline earth metal; and
separating the oxyfluoride material from the combined liquid compositions to provide the dental filler.

40. The method of claim 39 wherein the trivalent metal is selected from the group consisting of aluminum, lanthanum, and combinations thereof.

41. A method of preparing a dental filler comprising:
combining a first liquid composition comprising a source of aluminum and a source of an alkaline earth metal with a second liquid composition comprising a source of fluorine to provide an acid-reactive oxyfluoride material, wherein the oxyfluoride material comprises aluminum, oxygen, fluorine, and the alkaline earth metal; and
separating the oxyfluoride material from the combined liquid compositions to provide the dental filler.

42. The method of claim 41 wherein the oxyfluoride material is nanostructured.

43. The method of claim 41 wherein at least one of the liquid compositions further comprises a source of hydroxide as a source of oxygen.

44. The method of claim 43 wherein the source of hydroxide is selected from the group consisting of ammonium hydroxide, sodium hydroxide, potassium hydroxide, and combinations thereof.

45. The method of claim 41 wherein at least one of the liquid compositions is an aqueous composition having a pH greater than 7.

46. The method of claim 41 further comprising drying the separated oxyfluoride material at a temperature of at most 350° C.

47. The method of claim 46 wherein drying is at a temperature of at most 250° C.

48. The method of claim 47 wherein drying is at a temperature of at most 150° C.

49. The method of claim 41 wherein combining provides an oxyfluoride material in a form selected from the group consisting of a precipitate, a coating on a particle, a coating on an aggregate of particles, a material infiltrated in a porous structure, and combinations thereof.

50. The method of claim 41 wherein separating the oxyfluoride material comprises filtering the oxyfluoride material.

51. The method of claim 41 wherein the source of aluminum is selected from the group consisting of aluminum nitrates and basic or oxy salts thereof, aluminum carboxylates and basic or oxy salts thereof, aluminum halides and basic or oxy salts thereof, and combinations thereof.

52. The method of claim 41 wherein the source of aluminum comprises an aluminum alkoxide.

53. The method of claim 52 wherein the aluminum alkoxide is selected from the group consisting of aluminum isopropoxide, aluminum sec-butoxide, and combinations thereof.

54. The method of claim 41 wherein the source of fluorine is selected from the group consisting of ammonium fluoride, ammonium hydrogen difluoride, hexafluorosilicic acid and salts thereof, and combinations thereof.

55. The method of claim 41 wherein the source of the alkaline earth metal comprises strontium nitrates, strontium carboxylates, strontium halides, calcium nitrates, calcium carboxylates, calcium halides, and combinations thereof.

56. The method of claim 41 wherein the second liquid composition further comprises a source of silicon.

57. The method of claim 56 wherein the source of silicon comprises sodium silicate, hexafluorosilicic acid and salts thereof, silicon alkoxides, and combinations thereof.

58. The method of claim 41 wherein at least one of the first and second liquid compositions further comprises water.

59. The method of claim 41 further comprising dispersing the separated oxyfluoride material in a liquid medium.

60. The method of claim 59 wherein the liquid medium comprises water.

61. The method of claim 59 further comprising coating the dispersed oxyfluoride material on a particle, coating the dispersed oxyfluoride material on an aggregate of particles, infiltrating the dispersed oxyfluoride material in a porous structure, or combinations thereof.

62. A method of preparing a dental filler comprising:
providing a porous structure;
infiltrating a first liquid composition comprising a source of a trivalent metal and a source of an alkaline earth metal in the porous structure; and
infiltrating a second liquid composition comprising a source of fluorine in the porous structure to provide a porous structure infiltrated with an acid-reactive oxyfluoride material, wherein the acid-reactive oxyfluoride material comprises the trivalent metal, oxygen, fluorine, and the alkaline earth metal.

63. The method of claim 62 wherein the trivalent metal is selected from the group consisting of aluminum, lanthanum, and combinations thereof.

64. A method of preparing a dental filler comprising:
providing a porous structure;
infiltrating a first liquid composition comprising a source of aluminum and a source of an alkaline earth metal in the porous structure; and
infiltrating a second liquid composition comprising a source of fluorine in the porous structure to provide a porous structure infiltrated with an acid-reactive oxyfluoride material, wherein the acid-reactive oxyfluoride material comprises aluminum, oxygen, fluorine, and the alkaline earth metal.

65. The method of claim 64 further comprising drying the porous structure infiltrated with the acid-reactive oxyfluoride material at a temperature of at most 350° C.

66. The method of claim 64 wherein infiltrating the first liquid composition is carried out before infiltrating the second liquid composition.

67. The method of claim 64 wherein infiltrating the first liquid composition is carried out after infiltrating the second liquid composition.

68. The method of claim 64 wherein the second liquid composition further comprises a component selected from the group consisting of ammonium hydroxide, sodium hydroxide, potassium hydroxide, and combinations thereof.

69. The method of claim 64 wherein the second liquid composition further comprises a source of silicon.

70. The method of claim 64 wherein at least one of the first and second liquid compositions further comprises water.

71. The method of claim 64 wherein the porous structure is selected from the group consisting of porous particles, porous aggregates of particles, and combinations thereof.

72. A dental composition comprising a hardenable resin and a dental filler according to claim 1.

73. A dental composition comprising a hardenable resin and a dental filler according to claim 3.

74. The dental composition of claim 73 wherein the hardenable resin comprises a polymerizable ethylenically unsaturated compound.

75. The dental composition of claim 74 wherein the hardenable resin further comprises an acid.

76. The dental composition of claim 73 wherein the composition is in the form of a single-part dental composition.

77. The dental composition of claim 73 wherein the composition is in the form of a multi-part dental composition.

78. The dental composition of claim 77 wherein the multi-part composition comprises a first part and a second part, and wherein each part is independently selected from the group consisting of a liquid, paste, gel, or powder.

79. The dental composition of claim 77 wherein the multi-part composition is selected from the group consisting of a paste-paste composition, a paste-liquid composition, a paste-powder composition, and a powder-liquid composition.

80. The dental composition of claim 73 wherein the composition is selected from the group consisting of dental adhesives, cavity liners, cements, coatings, orthodontic adhesives, restoratives, sealants, and combinations thereof.

81. The dental composition of claim 73 wherein at least 90% by weight of the oxyfluoride material is nanostructured.

82. The dental composition of claim 81 further comprising a non acid-reactive filler.

83. The dental composition of claim 82 wherein at least 75% by weight of the total filler in the dental composition is nanofiller.

84. The dental composition of claim 82 wherein at least 90% by weight of the total filler in the dental composition is nanofiller.

85. The dental composition of claim 73 wherein the composition is in the form of a paste.

86. A dental composition comprising a hardenable resin and a dental filler according to claim 32.

87. The dental composition of claim 86 wherein the composition is in the form of a paste.

88. A dental composition comprising at most 15% by weight of a dental filler according to claim 1, with the proviso that the dental filler provides at least 2 square meters of surface area per gram of the dental composition.

89. A dental composition comprising:
at most 10% by weight of a dental filler according to claim 1, based on the total weight of the dental composition; and
at least 40% by weight of additional fillers, based on the total weight of the dental composition.

90. A method of preparing a dental composition comprising combining a dental filler according to claim 1 and a hardenable resin.

91. A method of preparing a dental composition comprising combining a dental filler according to claim 3 and a hardenable resin.

92. A method of preparing a dental composition comprising combining a dental filler according to claim 32 and a hardenable resin.

93. A dental composition comprising:
a dental filler according to claim 1;
a polyacid; and
water.

94. A dental composition comprising:
a dental filler according to claim 3;
a polyacid; and
water.

95. A multi-part dental composition comprising:
a part A comprising a dental filler according to claim 1; and
a part B comprising a polyacid.

96. A multi-part dental composition comprising:
a part A comprising a dental filler according to claim 3; and
a part B comprising a polyacid.

97. The multi-part dental composition of claim 96, wherein at least 90% by weight of the oxyfluoride material is nanostructured.

98. The multi-part dental composition of claim 96 wherein at least one of part A or part B further comprises an additional acid reactive filler.

99. The multi-part dental composition of claim 96 wherein at least one of part A or part B is in the form of a liquid or a paste.

100. The multi-part dental composition of claim 99 wherein part A and part B are provided in a unit-dose capsule.

101. The multi-part dental composition of claim 99 wherein part A and part B are each independently in the form of a liquid or a paste.

102. The multi-part dental composition of claim 101 further comprising a dual barrel syringe having a first barrel and a second barrel, wherein the part A resides in the first barrel and the part B resides in the second barrel.

103. The multi-part dental composition of claim 101 wherein part A and part B can be mixed in a static mixer.

104. The multi-part dental composition of claim 96 further comprising water residing in at least one of part A or part B.

105. The multi-part dental composition of claim 96 further comprising a polymerizable component residing in at least one of part A or part B.

106. The multi-part dental composition of claim 105 wherein the polyacid and the polymerizable component are the same.

107. The multi-part dental composition of claim 105 wherein the polyacid and the polymerizable component are different.

108. The multi-part dental composition of claim 96 further comprising a non acid-reactive dental filler residing in at least one of part A or part B.

109. The multi-part dental composition of claim 108 wherein at least 90% by weight of the non acid-reactive dental filler is in the form of nanoparticles.

110. The multi-part dental composition of claim 108 wherein the non acid-reactive dental filler comprises a metal oxide.

111. The multi-part dental composition of claim 110 wherein the metal oxide is silica.

112. A multi-part dental composition comprising:
a part A comprising an acid-reactive dental filler according to claim 32; and
a part B comprising at least one polyacid.

113. A method of using a multi-part dental composition according to claim 95 comprising:
mixing a quantity of part A and a quantity of part B to form a dental composition; and
applying the dental composition to a surface.

114. A method of preparing a dental article comprising:
combining a dental filler according to claim 1 and a hardenable resin to form a dental composition; and
hardening the composition to fabricate a dental article selected from the group consisting of crowns, fillings, mill blanks, orthodontic devices, and prostheses.

115. A method of preparing a dental article comprising:
combining a dental filler according to claim 3 and a hardenable resin to form a dental composition; and
hardening the composition to fabricate a dental article selected from the group consisting of crowns, fillings, mill blanks, orthodontic devices, and prostheses.

116. A method of preparing a dental article comprising:
combing a dental filler according to claim 32 and a hardenable resin to form a dental composition; and
hardening the composition to fabricate a dental article selected from the group consisting of crowns, fillings, mill blanks, orthodontic devices, and prostheses.

* * * * *

UNITED STATES PATENT AND TRADEMARK OFFICE
CERTIFICATE OF CORRECTION

PATENT NO. : 7,090,722 B2
APPLICATION NO. : 10/847805
DATED : August 15, 2006
INVENTOR(S) : Kenton D. Budd It is certified that error appears in the above-identified patent and that said Letters Patent is hereby corrected as shown below:

Title Page, Column 2:
Line 33, After "6,376,590" delete "B1" and insert -- B2 --, therefor.

Page 2, Column 1:
Line 12, After "6,693,143" delete "B1" and insert -- B2 --, therefor.
Line 14, After "6,696,507" delete "B1" and insert -- B2 --, therefor.

Page 2, Column 2:
Line 20, Delete "Infromation" and insert -- information --, therefor.
Line 22-23, Delete "(new York)," and insert -- (New York), --, therefor.
Line 23, After "No. 7," insert -- July 2002 --.

Column 1:
Line 60, Delete "coating," and insert -- coatings, --, therefor.

Column 6:
Line 33, Delete "Preparations" and insert -- Preparation --, therefor.

Column 9:
Line 15, Delete "be-monomeric," and insert -- be monomeric, --, therefor.
Line 56, Delete "are-listed" and insert -- are listed --, therefor.

Column 13:
Line 19, After "(Ying)." delete "P".
Line 19-38, After "(Ying). P" delete "Commercially available.........Charlotte, N.C" and insert the same on line 20 as a new paragraph.

Column 18:
Line 59, Delete "filer," and insert -- filler, --, therefor.

Column 21:
Line 37, Delete "Next-" and insert -- Next, --, therefor.

Column 23:
Line 59, Delete "Comprehensive" and insert -- Compressive --, therefor.

Column 28:
Line 36, Delete "Materials" and insert -- Material --, therefor.

Column 29:
Line 30, After "each" insert -- of --.

UNITED STATES PATENT AND TRADEMARK OFFICE
CERTIFICATE OF CORRECTION

PATENT NO. : 7,090,722 B2
APPLICATION NO. : 10/847805
DATED : August 15, 2006
INVENTOR(S) : Kenton D. Budd It is certified that error appears in the above-identified patent and that said Letters Patent is hereby corrected as shown below:

<u>Column 30:</u>
Line 15, Delete "$Al(OH)_{0.75}(F)_{0.75})$" and insert -- $Al(OH)_{0.75}(F)_{0.75}$ --, therefor.

<u>Column 32:</u>
Line 41, Delete "(Example 16-18)" and insert -- (Examples 16-18) --, therefor.

<u>Column 35:</u>
Line 21, Delete "(parts by weight)" and insert -- (Parts by Weight) --, therefor.
Line 23, Delete "Dl H2O" and insert -- Dl $H_2O$ --, therefor.

<u>Column 35-36:</u>
Starting Line 52, Delete "BisGMAUDMA" and insert -- BisGMA/UDMA --, therefor.

<u>Column 36:</u>
Table 5B, Line 6, Delete "bisGMA" and insert -- BisGMA --, therefor.

<u>Column 37:</u>
Line 39, Delete "Composition" and insert -- Compositions --, therefor.

<u>Column 46:</u>
Line 39, In Claim 116, delete "combging" and insert -- combining --, therefor.

Signed and Sealed this

Twenty-fifth Day of September, 2007

JON W. DUDAS
*Director of the United States Patent and Trademark Office*